(12) United States Patent
Hill et al.

(10) Patent No.: US 10,900,035 B2
(45) Date of Patent: Jan. 26, 2021

(54) PRNA THREE-WAY JUNCTIONS

(71) Applicants: The Board of Regents of the University of Oklahoma, Norman, OK (US); Alyssa C. Hill, Zurich (CH)

(72) Inventors: Alyssa C. Hill, Zurich (CH); Susan J. Schroeder, Norman, OK (US)

(73) Assignees: The Board of Regents of the University of Oklahoma, Norman, OK (US); Alyssa C. Hill, Zurich (CH)

( * ) Notice: Subject to any disclaimer, the term of this patent is extended or adjusted under 35 U.S.C. 154(b) by 123 days.

(21) Appl. No.: 16/079,476

(22) PCT Filed: Feb. 26, 2017

(86) PCT No.: PCT/US2017/019556
§ 371 (c)(1),
(2) Date: Aug. 23, 2018

(87) PCT Pub. No.: WO2017/147557
PCT Pub. Date: Aug. 31, 2017

(65) Prior Publication Data
US 2019/0055551 A1    Feb. 21, 2019

Related U.S. Application Data

(60) Provisional application No. 62/300,517, filed on Feb. 26, 2016.

(51) Int. Cl.
C12N 15/113    (2010.01)
C12N 15/11     (2006.01)

(52) U.S. Cl.
CPC ........ *C12N 15/111* (2013.01); *C12N 2310/14* (2013.01); *C12N 2310/16* (2013.01); *C12N 2310/3519* (2013.01); *C12N 2310/52* (2013.01); *C12N 2320/32* (2013.01)

(58) Field of Classification Search
None
See application file for complete search history.

(56) References Cited

U.S. PATENT DOCUMENTS

2014/0179758 A1    6/2014    Guo

FOREIGN PATENT DOCUMENTS

WO    WO-2015/196146 A2    12/2015

OTHER PUBLICATIONS

Shu et al., "Thermodynamically Stable RNA three-way junctions as platform for constructing multi-functional naoparticles for delivery of therapeutics", Nat Nanotechnol, vol. 6, Sep. 11, 2011, 19 paged.
Zhang et al., "Crystal structure of 3WJ core revealing divalent ion-promoted thermostability and assembly of the Phi29 hexameric motor pRNA", RNA, vol. 19, Jul. 24, 2013, pp. 1226-1237.
Hill et al., "Thermodynamic stabilities of three-way junction nanomotifs in prohead RNA", RNA, vol. 23, Jan. 9, 2017, pp. 521-529.
International Search Report, dated Jun. 22, 2017, Blaine R. Copenheaver.
Written Opinion of the International Search Authority, dated Jun. 22, 2017, Blaine R. Copenheaver.
Binzel, Daniel W. et al.; "Entropy-Driven One-Step Formation of Phi29 pRNA 3WJ from Three RNA Fragments"; Biochemistry; vol. 53; 2014; pp. 2221-2231.
Chistol, Gheorghe et al.; "High Degree of Coordination and Division of Labor among Subunits in a Homomeric Ring ATPase"; Cell; 151(5); Nov. 21, 2012; 23 pages.
Ding, Fang et al.; "Structure and assembly of the essential RNA ring component of a viral DNA packaging motor"; PNAS; vol. 108 No. 18; May 3, 2011; pp. 7357-7362.
Gu, Xiaobo et al.; "Different Sequences Show Similar Quaternary Interaction Stabilities in Prohead Viral RNA Self-assembly"; Journal of Biological Chemistry; vol. 286 No. 16; Apr. 22, 2011; pp. 14419-14426.
Guo, Peixuan et al.; "A Small Viral RNA Is Required for in Vitro Packaging of Bacteriophage φ29 DNA"; Science; vol. 236; May 8, 1987; pp. 690-694.
Guo, Peixuan; "The emerging field of RNA nanotechnology"; Nature Nanotechnology; vol. 5; Dec. 2010; pp. 833-842.
Guo, S et al.; "Construction of folate-conjugated pRNA of bacteriophage phi29 DNA packaging motor for delivery of chimeric siRNA to nasopharyngeal carcinoma cells"; Gene Therapy; vol. 13; 2006; pp. 814-820.
Guo, Songchuan et al.; "Specific Delivery of Therapeutic RNAs to Cancer Cells via the Dimerization Mechanism of phi29 Motor pRNA"; Human Gene Therapy; No. 16(9); Sep. 2005; 22 pages.
Hao, Yumeng et al; "Diverse self-association properties within a family of phage packaging RNAs"; RNA; vol. 20 No. 11; Feb. 26, 2016; 16 pages.
Hague, Farzin et al.; "Ultrastable synergistic tetravalent RNA nanoparticles for targeting cancers"; Nano Today; vol. 7; 2012; pp. 245-257.
Ibarra, Borja et al.; "Topology of the Components of the DNA Packaging Machinery in the Phage φ29 Prohead"; J. Mol. Biol.; No. 298; 2000; pp. 807-815.
Ko, Seung Hyeon et al; "Synergistic self-assembly of RNA and DNA molecules"; Nature Chemistry; vol. 2; Dec. 2010; pp. 1050-1055.

(Continued)

*Primary Examiner* — Kimberly Chong
(74) *Attorney, Agent, or Firm* — Winstead PC

(57) ABSTRACT

Three-way junction (3WJ) RNA scaffolds derived from phi29, M2, SF5, and GA1 pRNAs and which have high stability are described. The pRNA 3WJ scaffolds can be used to form compounds, conjugates, compositions, and nanoparticles for delivery of active agents for therapeutic and/or diagnostic functions.

12 Claims, 33 Drawing Sheets

Specification includes a Sequence Listing.

(56) References Cited

OTHER PUBLICATIONS

Li, Li et al.; "Evaluation of specific delivery of chimeric phi29 pRNA/siRNA nanoparticles to multiple tumor cells"; Molecular BioSystems; No. 5; 2009; pp. 1361-1368.

Moffitt, Jeffrey R. et al; "Intersubunit coordination in a homomeric ring ATPase"; Nature; vol. 457; Jan. 22, 2009; pp. 446-451.

Morais, Marc C. et al.; "Defining Molecular and Domain Boundaries in the Bacteriophage φ29 DNA Packaging Motor"; Structure; No. 16; Aug. 6, 2008; pp. 1267-1274.

Schroeder, Susan J. et al.; "Optical Melting Measurements of Nucleic Acid Thermodynamics"; Methods Enzymol; Jun. 25, 2014; 15 pages.

Shu, Dan et al.; "Thermodynamically stable RNA three-way junction for constructing multifunctional nanoparticles for delivery of therapeutics"; Nature Nanotechnology; vol. 6; Oct. 2011; pp. 658-667.

Shu, Dan et al.; "Bottom-up Assembly of RNA Arrays and Superstructures as Potential Parts in Nanotechnology"; Nano Letters; vol. 4 No. 9; 2004; pp. 1717-1723.

Shu, Yi et al.; "Assembly of multifunctional phi29 pRNA nanarticles for specific delivery of siRNA and other therapeutics to targeted cells"; Methods; No. 54; 2011; pp. 204-214.

Shu, Yi et al.; "Fabrication of 14 different RNA nanoparticles for specific tumor targeting without accumulation in normal organs"; RNA; vol. 19 No. 6; 2013; pp. 767-777.

Shu, Yi et al.; "Fabrication of pRNA nanoparticles to deliver therapeutic RNAs and bioactive compounds into tumor cells"; Nature Protocols; vol. 8 No. 9; 2013; pp. 1635-1659.

Singh, Yashveer et al.; "Recent developments in oligonucleotide conjugation"; Chemical Society Reviews; No. 39; 2010; pp. 2054-2070.

Turner, Douglas H. et al.; "NNDB: the nearest neighbor parameter database for predicting stability of nucleic acid secondary structure"; Nucleic Acids Research; vol. 38; 2010; pp. D280-D282.

Wichitwechkarn, Jesdawan et al.; "Prohead RNA of bacteriophage φ29: size, stoichiometry and biological activity"; Nucleic Acids Research; vol. 17 No. 9; 1989; pp. 3459-3468.

Zhang, Hui et al; "Crystal structure of 3WJ core revealing divalent ion-promoted thermostability and assembly of the Phi29 hexameric motor pRNA"; RNA; vol. 19 No. 9; 2013; pp. 1226-1237.

```
5'- CUUGUCAUG  GUAUGUUGCC - 3'
3'- GAACGGUAC  CAUAC  ACGG - 5'
            |  U
            U G
            A U
            A U
            C G
            U A
            G U
            U A
            C G
            C G
            | |
            5' 3'
```

FIG. 12

```
5'- CUUGUCAUG  GUAUGUUGCC - 3'
3'- GAACGGUAC  CAUAC  ACGG - 5'
            U G
            A U
            A U
            C G
            U A
            G U
            U A
            C G
            C G
            | |
            5' 3'
```

FIG. 13

```
5'- UUGUCAUG  GUAUGUUGC - 3'
3'- AACGGUAC  CAUAC  ACG - 5'
             |     U
             U G
             A U
             A U
             C G
             U A
             G U
             U A
             C G
             | |
             5' 3'
```

FIG. 17

```
5'- UGUCAUG  GUAUGUUGC - 3'
3'- ACGGUAC  CAUAC  ACG - 5'
            |     U
            U G
            A U
            A U
            C G
            U A
            G U
            U A
            C G
            | |
            5' 3'
```

FIG. 18

```
5'- UGUCAUG  GUAUGUUG - 3'
3'- ACGGUAC  CAUAC   AC - 5'
              |  U
              U  G
              A  U
              A  U
              C  G
              U  A
              G  U
              U  A
              C  G
              |  |
              5' 3'
```

FIG. 19

```
5'- UGUCAUG  GUAUGUUG - 3'
3'- ACGGUAC  CAUAC   AC - 5'
              |  U
              U  G
              A  U
              A  U
              C  G
              U  A
              G  U
              U  A
              |  |
              5' 3'
```

FIG. 20

```
5'- GUCAUG GUAUGUUG - 3'
3'- CGGUAC CAUAC  AC - 5'
          | U
          U G
          A U
          A U
          C G
          U A
          G U
          U A
          | |
          5' 3'
```

FIG. 21

```
5'- GUCAUG GUAUGUU - 3'
3'- CGGUAC CAUAC  A - 5'
          | U
          U G
          A U
          A U
          C G
          U A
          G U
          U A
          | |
          5' 3'
```

FIG. 22

```
5'- UCAUG GUAUG - 3'
3'- GGUAC CAUAC - 5'
       |  U
       U  G
       A  U
       A  U
       C  G
       U  A
       G  U
       |  |
       5' 3'
```

FIG. 25

```
5'- UCAUG GUAUG - 3'
3'- GGUAC CAUAC - 5'
       |  U
       U  G
       A  U
       A  U
       C  G
       U  A
       |  |
       5' 3'
```

FIG. 26

```
CAAUAGUA   UGGCACAUGUG
GUUAUCAU   ACU    GUACAC
        U  C
        C
         UG
         CG
         CG
         CG
         AU
         UA
         CG
```

FIG. 27

```
AAUAGUA    UGGCACAUGU
UUAUCAU    ACU    GUACA
        U  C
        C
         UG
         CG
         CG
         CG
         AU
         UA
```

FIG. 28

```
AUAGUA    UGGCACAUG
UAUCAU    ACU    GUAC
       U  C
       C
        UG
        CG
        CG
        CG
```

FIG. 29

```
UAGUA   UGGCACA
AUCAU   ACU   GU
    U C
    C
    UG
    CG
    CG
    CG
```

FIG. 30

```
AGUA   UGGCAC
UCAU   ACU   G
    U C
    C
    UG
    CG
    CG
```

FIG. 31

```
5' - GCUAAUGUA   UGUUGUCCG - 3'
3' - CGAUUACGU   ACGACAGGC - 5'
              | G
              | G
              UG
              CG
              UA
              CG
              AC
              CG
              AU
              CG
              GC
              | |
              5' 3'
```

FIG. 32

```
5' - GCUAAUGUA   UGUGUGUCCG – 3'
3' - CGAUUACGU   ACG   ACAGGC - 5
               |  G
               UG
               CG
               UA
               CG
               AC
               CG
               AU
               CG
               GC
               | |
               5' 3'
```

FIG. 37

```
5' - CUAAUGUA   UGUGUGUCC – 3'
3' - GAUUACGU   ACG   ACAGG - 5
              |  G
              UG
              CG
              UA
              CG
              AC
              CG
              AU
              CG
              | |
              5' 3'
```

FIG. 38

```
5' - UAAUGUA   UGUGUGUC - 3'
3' - AUUACGU   ACG   ACAG - 5
             | G
             UG
             CG
             UA
             CG
             AC
             CG
             AU
             | |
             5' 3'
```

FIG. 39

```
5' - AAUGUA   UGUGUGU - 3'
3' - UUACGU   ACG   ACA - 5
            | G
            UG
            CG
            UA
            CG
            AC
            CG
            | |
            5' 3'
```

FIG. 40

```
5' - AUGUA    UGUGUG – 3'
3'- UACGU   ACG   AC - 5'
           |  G
           UG
           CG
           UA
           CG
           AC
           | |
           5' 3'
```

FIG. 41

```
5' - GCUAAUGUA    UGUUGUCCG – 3'
3'- CGAUUACGU    ACGACAGGC - 5'
              |  G
              UG
              CG
              UA
              CG
              AC
              CG
              AU
              CG
              GC
              | |
              5' 3'
```

FIG. 42

```
5' -  CUAAUGUA    UGUUGUCC - 3'
3' -  GAUUACGU    ACGACAGG - 5'
               |  G
               UG
               CG
               UA
               CG
               AC
               CG
               AU
               CG
               |  |
               5' 3'
```

FIG. 43

```
5' - UAAUGUA    UGUUGUC - 3'
3' - AUUACGU    ACGACAG - 5'
              |  G
              U G
              C G
              U A
              CG
              A C
              C G
              A U
              |  |
              5' 3'
```

FIG. 44

```
5' - UAUAG G  CUGUGCA - 3'
3' - AUAUC    GACA  GU - 5'
          A  |
          U G
          A U
          A U
          C G
          G U
          |  |
          5' 3'
```

FIG. 47

```
5' - WWWWW  WWWWW - 3'
3' - C C C C C  C C C C C - 5'
         |     N
         W     C
         W     C
         W     C
         W     C
         W     C
         |     |
         5'    3'
```

FIG. 48

PRNA THREE-WAY JUNCTIONS

CROSS-REFERENCE TO RELATED APPLICATIONS

This application is a national stage application of PCT/US2017/019556, which claims priority to U.S. Provisional Application No. 62/300,517, filed on Feb. 26, 2016, which is expressly incorporated herein by reference in its entirety.

GOVERNMENT SUPPORT

This invention was made with government support under Grant Numbers 2012174160 and 0844913 awarded by the National Science Foundation. The government has certain rights in the invention.

BACKGROUND

Previous studies have demonstrated that packaging (or prohead) ribonucleic acid (pRNA) three-way junction (3WJ) motifs have applications in biotechnology, such as in targeting of human immunodeficiency virus (HIV) and cancer. For example, the phi29 bacteriophage pRNA 3WJ nanomotif has been extensively studied and successfully used as a building block in the rational design of nanostructures with, for example cancer targeting functionalities (e.g., see U.S. Pat. No. 9,297,013 B2).

BRIEF DESCRIPTION OF THE DRAWINGS

Several embodiments of the present disclosure are hereby illustrated in the appended drawings. It is to be noted however, that the appended drawings only illustrate several embodiments and are therefore not intended to be considered limiting of the scope of the present disclosure.

Figure 11:
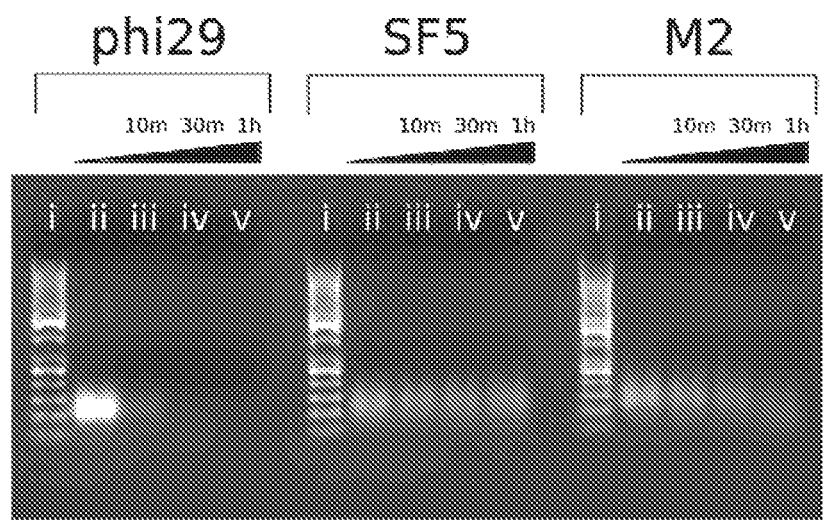
Figure 14:
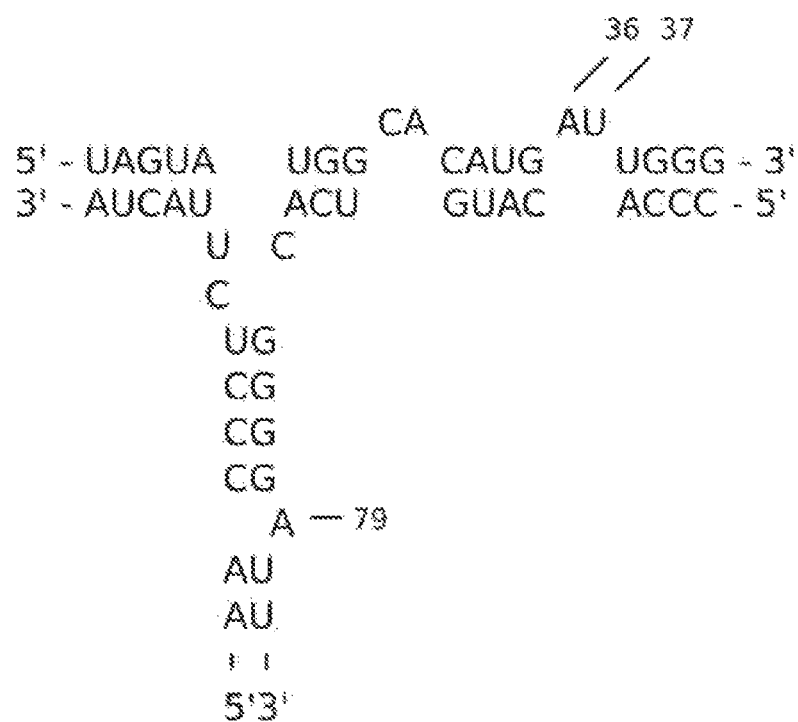
Figure 15:
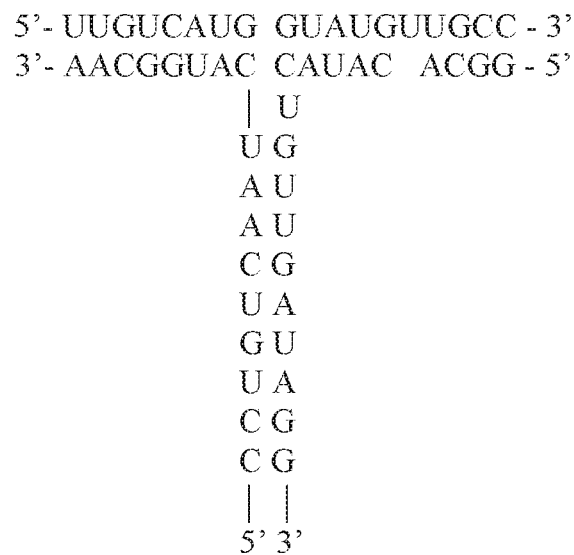
Figure 16:
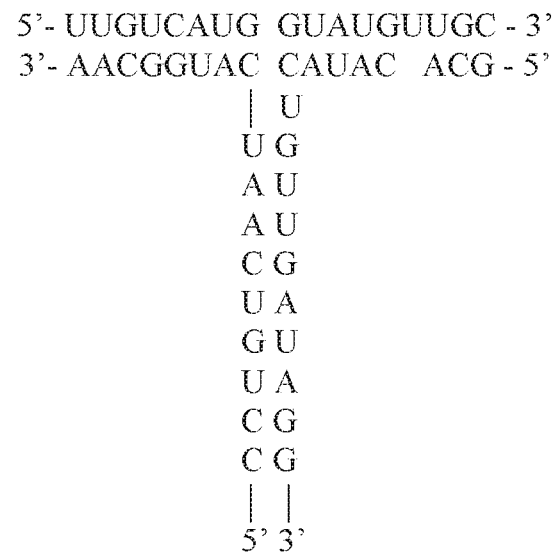
Figure 23:
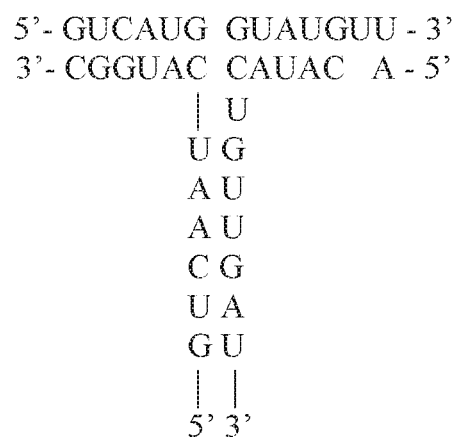
Figure 24:
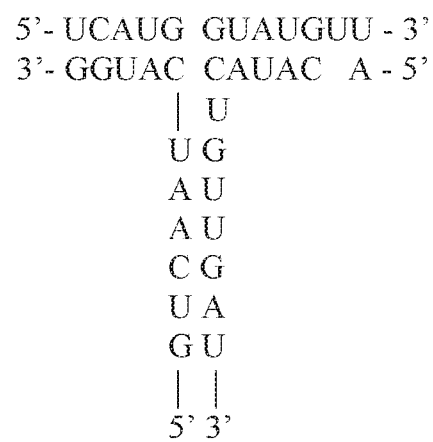
Figure 33:
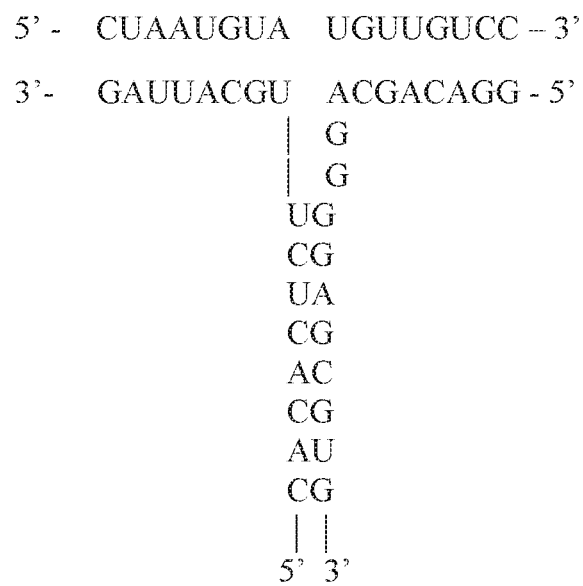
Figure 34:
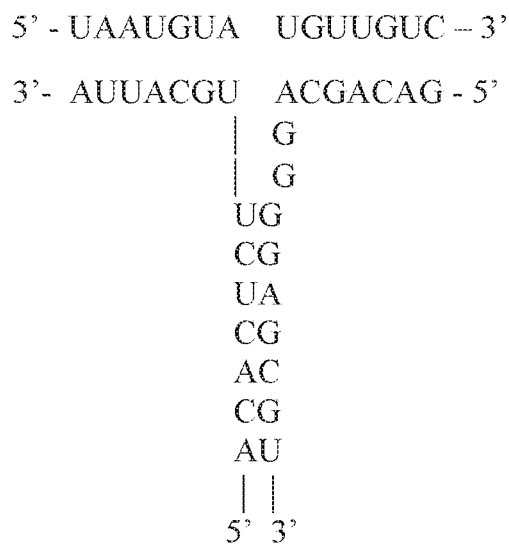
Figure 35:
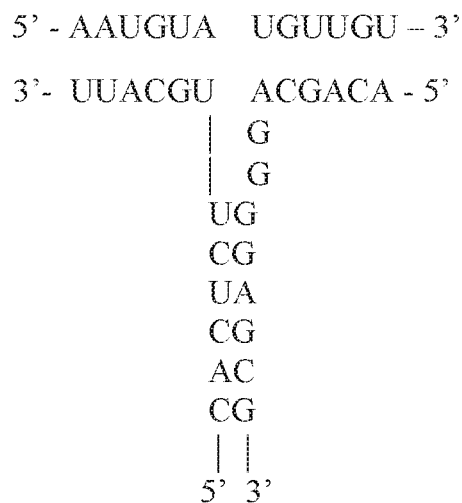
Figure 36:
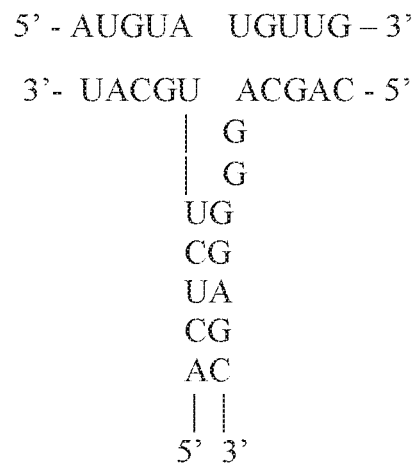
Figure 45:
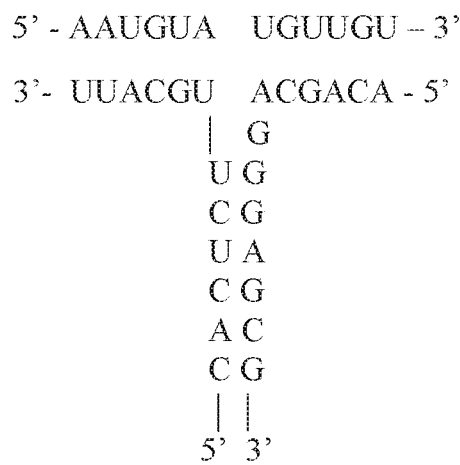
Figure 46:
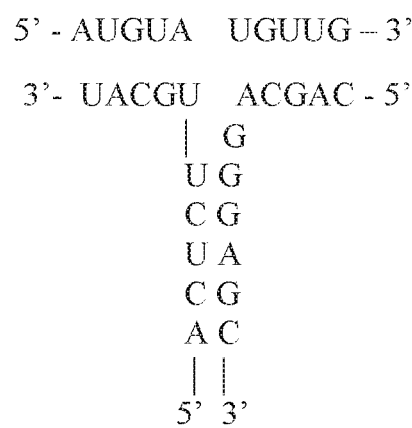
Figure 49:
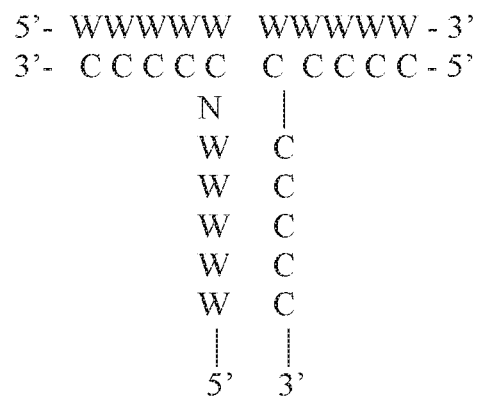
Figure 50:
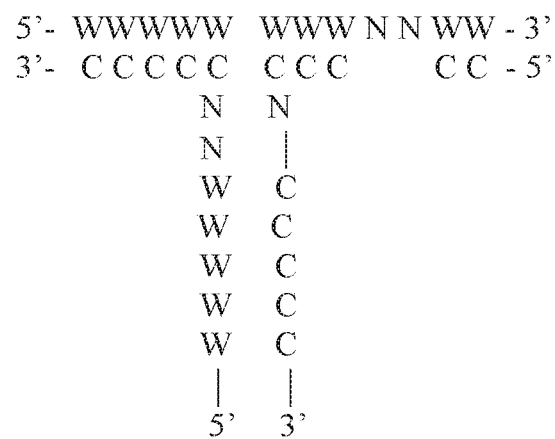
Figure 51:
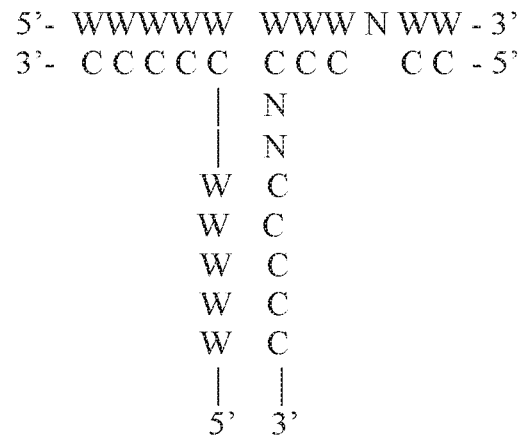
Figure 52:
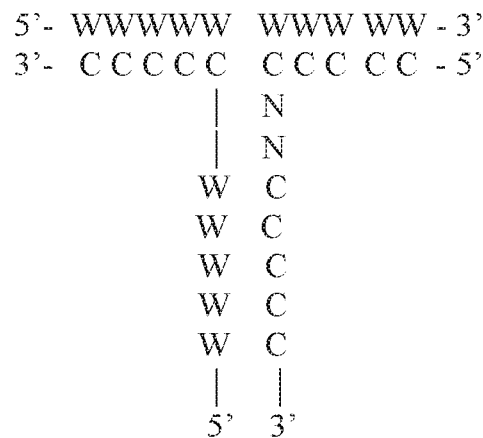
Figure 53:
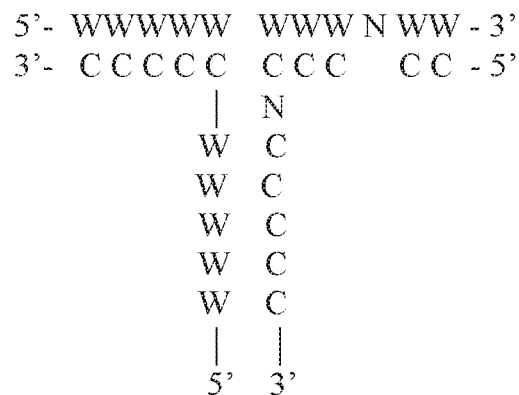
Figure 54:
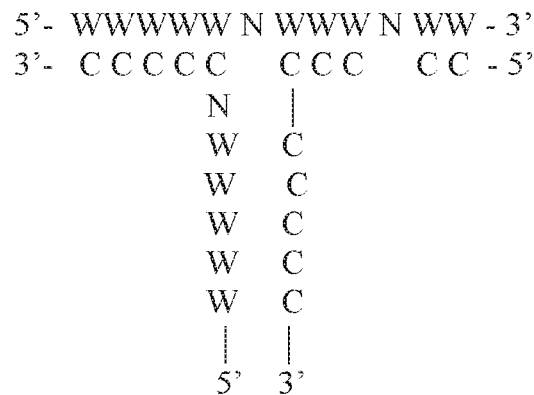

Lane (i) 50 bp DNA ladder, (ii) phi29 3WJ construct in standard melt buffer (negative degradation control), (iii) phi29 3WJ construct, (iv) M2 3WJ construct, (v) SF5 3WJ construct, (vi) SF5$_{\Delta G31}$ 3 WJ construct, (vii) SF5$_{\Delta G69}$ 3 WJ construct, (viii) SF5$_{\Delta G31/\Delta G69}$ 3WJ construct;

FIG. 11 shows a comparison of the gel mobility of 10 μM phi29, SF5, and M2 assembled 3WJ constructs in 2% (w/v) agarose stained with ethidium bromide in TAE buffer following exposure to 1000-fold diluted human blood serum for 10 minutes, 30 minutes, and 1 hour. All reactions were carried out at 37° C. Lane (i) 50 bp DNA ladder, (ii) 3WJ construct in standard melt buffer (1 M sodium chloride, 10 mM sodium cacodylate, 0.5 EDTA, pH 7) for 1 hour (negative degradation control), (iii) 3WJ construct in 1000-fold diluted serum for 10 minutes, (iv) 3WJ construct in 1000-fold diluted serum for 30 minutes, (v) 3WJ construct in 1000-fold diluted serum for 1 hour;

FIG. 12 depicts a mutant phi29 pRNA 3WJ construct (phi29$_{\Delta U29/\Delta U72-73}$) according to the present disclosure;

FIG. 13 depicts an alternate mutant phi29 pRNA 3WJ construct (phi29$_{\Delta U29/\Delta U72-73-74}$) according to the present disclosure;

FIG. 14 depicts a pRNA 3WJ construct derived from wild type M2 having unpaired nucleotides at positions 36, 37 and 79;

FIG. 15 depicts a truncated mutant phi29 pRNA 3WJ construct (phi29$_{\Delta U29/\Delta U72-73}$) according to the present disclosure;

FIG. 16 depicts an alternate truncated mutant phi29 pRNA 3WJ construct (phi29$_{\Delta U29/\Delta U72-73}$) according to the present disclosure;

FIG. 17 depicts an alternate truncated mutant phi29 pRNA 3WJ construct (phi29$_{\Delta U29/\Delta U72-73}$) according to the present disclosure;

FIG. 18 depicts an alternate truncated mutant phi29 pRNA 3WJ construct (phi29$_{\Delta U29/\Delta U72-73}$) according to the present disclosure;

FIG. 19 depicts an alternate truncated mutant phi29 pRNA 3WJ construct (phi29$_{\Delta U29/\Delta U72-73}$) according to the present disclosure;

FIG. 20 depicts an alternate truncated mutant phi29 pRNA 3WJ construct (phi29$_{\Delta U29/\Delta U72-73}$) according to the present disclosure;

FIG. 21 depicts an alternate truncated mutant phi29 pRNA 3WJ construct (phi29$_{\Delta U29/\Delta U72-73}$) according to the present disclosure;

FIG. 22 depicts an alternate truncated mutant phi29 pRNA 3WJ construct (phi29$_{\Delta U29/\Delta U72-73}$) according to the present disclosure;

FIG. 23 depicts an alternate truncated mutant phi29 pRNA 3WJ construct (phi29$_{\Delta U29/\Delta U72-73}$) according to the present disclosure;

FIG. 24 depicts an alternate truncated mutant phi29 pRNA 3WJ construct (phi29$_{\Delta U29/\Delta U72-73}$) according to the present disclosure;

FIG. 25 depicts an alternate truncated mutant phi29 pRNA 3WJ construct (phi29$_{\Delta U29/\Delta U72-73}$) according to the present disclosure;

FIG. 26 depicts an alternate truncated mutant phi29 pRNA 3WJ construct (phi29$_{\Delta U29/\Delta U72-73}$) according to the present disclosure;

FIG. 27 depicts a mutant M2 pRNA 3WJ construct (M2$_{\Delta A36U37/A79}$) according to the present disclosure;

FIG. 28 depicts a truncated mutant M2 pRNA 3WJ construct (M2$_{\Delta A36U37/A79}$) according to the present disclosure;

FIG. 29 depicts an alternate truncated mutant M2 pRNA 3WJ construct (M2$_{\Delta A36U37/A79}$) according to the present disclosure;

FIG. 30 depicts an alternate truncated mutant M2 pRNA 3WJ construct (M2$_{\Delta A36U37/A79}$) according to the present disclosure;

FIG. 31 depicts an alternate truncated mutant M2 pRNA 3WJ construct (M2$_{\Delta A36U37/A79}$) according to the present disclosure;

FIG. 32 depicts a mutant SF5 pRNA 3WJ construct (SF5$_{\Delta G31}$) according to the present disclosure;

FIG. 33 depicts a truncated mutant SF5 pRNA 3WJ construct (SF5$_{\Delta G31}$) according to the present disclosure;

FIG. 34 depicts an alternate truncated mutant SF5 pRNA 3WJ construct (SF5$_{\Delta G31}$) according to the present disclosure;

FIG. 35 depicts an alternate truncated mutant SF5 pRNA 3WJ construct (SF5$_{\Delta G31}$) according to the present disclosure;

FIG. 36 depicts an alternate truncated mutant SF5 pRNA 3WJ construct (SF5$_{\Delta G31}$) according to the present disclosure;

FIG. 37 depicts a mutant SF5 pRNA 3WJ construct (SF5$_{\Delta G69}$) according to the present disclosure;

FIG. 38 depicts a truncated mutant SF5 pRNA 3WJ construct (SF5$_{\Delta G69}$) according to the present disclosure;

FIG. 39 depicts an alternate truncated mutant SF5 pRNA 3WJ construct (SF5$_{\Delta G69}$) according to the present disclosure;

FIG. 40 depicts an alternate truncated mutant SF5 pRNA 3WJ construct (SF5$_{\Delta G69}$) according to the present disclosure;

FIG. 41 depicts an alternate truncated mutant SF5 pRNA 3WJ construct (SF5$_{\Delta G69}$) according to the present disclosure;

FIG. 42 depicts a mutant SF5 pRNA 3WJ construct (SF5$_{\Delta G31/\Delta G69}$) according to the present disclosure;

FIG. 43 depicts a truncated mutant SF5 pRNA 3WJ construct (SF5$_{\Delta G31/\Delta G69}$) according to the present disclosure;

FIG. 44 depicts an alternate truncated mutant SF5 pRNA 3WJ construct (SF5$_{\Delta G31/\Delta G69}$) according to the present disclosure;

FIG. 45 depicts an alternate truncated mutant SF5 pRNA 3WJ construct (SF5$_{\Delta G31/\Delta G69}$) according to the present disclosure;

FIG. 46 depicts an alternate truncated mutant SF5 pRNA 3WJ construct (SF5$_{\Delta G31/\Delta G69}$) according to the present disclosure;

FIG. 47 depicts a GA1 pRNA 3WJ construct according to the present disclosure;

FIG. 48 depicts a generic mutant phi29 pRNA 3WJ construct according to the present disclosure. W and C represent paired nucleotides and N in the 3WJb strand represents an unpaired nucleotide;

FIG. 49 depicts a generic mutant phi29 pRNA 3WJ construct according to the present disclosure. W and C represent paired nucleotides and N in the 3WJc strand represents an unpaired nucleotide;

FIG. 50 depicts a generic mutant M2 pRNA 3WJ construct according to the present disclosure. W and C represent paired nucleotides and Ns in the 3WJa, 3WJb, and 3WJc strands represent unpaired nucleotides;

FIG. 51 depicts a generic mutant SF5 pRNA 3WJ construct according to the present disclosure. W and C represent paired nucleotides and Ns in the 3WJa and 3WJb strands represent unpaired nucleotides;

FIG. 52 depicts a generic mutant SF5 pRNA 3WJ construct according to the present disclosure. W and C represent paired nucleotides and the Ns in the 3WJb strand represent unpaired nucleotides;

FIG. 53 depicts a generic mutant SF5 pRNA 3WJ construct according to the present disclosure. W and C represent paired nucleotides and Ns in the 3WJa and 3WJb strands represent unpaired nucleotides; and FIG. 54 depicts a generic mutant GA1 pRNA 3WJ construct according to the present disclosure. W and C represent paired nucleotides and Ns in the 3WJa and 3WJc strands represent unpaired nucleotides.

DETAILED DESCRIPTION

One obstacle to using RNA nanomotifs such as pRNA 3WJs as building blocks in the rational design of diagnostics and therapeutics has been their characteristic low stability. Disclosed herein are novel trifurcate pRNA 3WJ motifs and methods of their use to construct compounds which can be used in therapeutic and biotechnology applications, including, but not limited to, therapeutic delivery, diagnosis of diseases, promotion of RNA crystallization, or creation of stable RNA aptamers. The stability of the novel 3WJs contributes to the self-assembly properties of pRNA. Thus pRNA 3WJ motifs disclosed herein indicate new scaffolds for pRNA-based nanotechnology.

Using a three-component RNA system designed for UV optical melting, the thermodynamic parameters of eleven pRNA 3WJs, including seven mutated phi29 pRNA 3WJs, were measured. The results, discussed further below, show that certain 3WJs such as the GA1, SF5, and M2 pRNA 3WJs described herein have greater thermodynamic stability than the stem phi29 pRNA 3WJ commonly used as a scaffold in RNA-based nanotechnology. Furthermore, certain deletions in the phi29 pRNA 3WJ are shown to increase its stability relative to the stem phi29 pRNA 3WJ. Further, metal ions are shown to have a differential stabilizing effect on pRNA 3WJs.

Before further describing various embodiments of the trifurcate pRNA 3WJ constructs, nanoparticles, compounds, compositions, and methods of the present disclosure in more detail by way of exemplary description, examples, and results, it is to be understood that the constructs, nanoparticles, compounds, compositions, and methods of present disclosure are not limited in application to the details of specific embodiments and examples as set forth in the following description. The description provided herein is intended for purposes of illustration only and is not intended to be construed in a limiting sense. As such, the language used herein is intended to be given the broadest possible scope and meaning; and the embodiments and examples are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the present disclosure. However, it will be apparent to a person having ordinary skill in the art that the present disclosure may be practiced without these specific details. In other instances, features which are well known to persons of ordinary skill in the art have not been described in detail to avoid unnecessary complication of the description. It is intended that all alternatives, substitutions, modifications and equivalents apparent to those having ordinary skill in the art are included within the scope of the present disclosure. All of the constructs, nanoparticles, compounds, compositions, and methods of production and application and use thereof disclosed herein can be made and executed without undue experimentation in light of the present disclosure. Thus, while the constructs, nanoparticles, compounds, compositions, and methods of the present disclosure have been described in terms of particular embodiments, it will be apparent to those of skill in the art that variations may be applied to the constructs, nanoparticles, compounds, compositions and/or methods and in the steps or in the sequence of steps of the methods described herein without departing from the concept, spirit, and scope of the inventive concepts.

All patents, published patent applications, and non-patent publications mentioned in the specification or referenced in any portion of this application, including U.S. Pat. Nos. 9,297,013, 8,088,912, and U.S. Provisional Patent Application No. 62/300,517, are herein expressly incorporated by reference in their entirety to the same extent as if each individual patent or publication was specifically and individually indicated to be incorporated by reference.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular. Where used herein, the specific term "single" is limited to only "one".

As utilized in accordance with the methods, compounds, and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment and may be included in other embodiments. The appearances of the phrase "in one embodiment" in various places in the specification are not necessarily all referring to the same embodiment and are not necessarily limited to a single or particular embodiment.

The term "pharmaceutically acceptable" refers to compounds and compositions which are suitable for administration to humans and/or animals without undue adverse side effects such as toxicity, irritation and/or allergic response commensurate with a reasonable benefit/risk ratio. The compounds or conjugates of the present disclosure may be combined with one or more pharmaceutically-acceptable excipients, including carriers, vehicles, and diluents which may improve solubility, deliverability, dispersion, stability, and/or conformational integrity of the compounds or conjugates thereof.

By "biologically active" it is meant the ability of an active agent to modify the physiological system of an organism without reference to how the active agent has its physiological effects.

As used herein, "pure," or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

Non-limiting examples of animals within the scope and meaning of this term include dogs, cats, rats, mice, guinea pigs, chinchillas, horses, goats, cattle, sheep, zoo animals, Old and New World monkeys, non-human primates, and humans.

"Treatment" refers to therapeutic treatments. "Prevention" refers to prophylactic or preventative treatment measures or reducing the onset of a condition or disease. The term "treating" refers to administering the composition to a subject for therapeutic purposes and/or for prevention.

The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of an active agent which is sufficient to exhibit a detectable therapeutic or treatment effect in a subject without excessive adverse side effects (such as substantial toxicity, irritation and allergic response) commensurate with a reasonable benefit/risk ratio when used in the manner of the present disclosure. The effective amount for a subject will depend upon the subject's type, size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "ameliorate" means a detectable or measurable improvement in a subject's condition, disease or symptom thereof. A detectable or measurable improvement includes a subjective or objective decrease, reduction, inhibition, suppression, limit or control in the occurrence, frequency, severity, progression, or duration of the condition or disease, or an improvement in a symptom or an underlying cause or a consequence of the disease, or a reversal of the disease. A successful treatment outcome can lead to a "therapeutic effect," or "benefit" of ameliorating, decreasing, reducing, inhibiting, suppressing, limiting, controlling or preventing the occurrence, frequency, severity, progression, or duration of a disease or condition, or consequences of the disease or condition in a subject.

A decrease or reduction in worsening, such as stabilizing the condition or disease, is also a successful treatment outcome. A therapeutic benefit therefore need not be complete ablation or reversal of the disease or condition, or any one, most or all adverse symptoms, complications, consequences or underlying causes associated with the disease or condition. Thus, a satisfactory endpoint may be achieved when there is an incremental improvement such as a partial decrease, reduction, inhibition, suppression, limit, control or prevention in the occurrence, frequency, severity, progression, or duration, or inhibition or reversal of the condition or disease (e.g., stabilizing), over a short or long duration of time (hours, days, weeks, months, etc.). Effectiveness of a method or use, such as a treatment that provides a potential therapeutic benefit or improvement of a condition or disease, can be ascertained by various methods and testing assays.

Where used herein, the term "three-way junction" ("3WJ") or "trifurcate" scaffold (or domain) refers to a pRNA construct assembled from three RNA sequences. The pRNA 3WJ is constructed from three (5'→3') strands of RNA (referred to as 3WJa, 3WJb, and 3WJc as represented in FIG. 1) which base pair when mixed in equimolar concentrations. More particularly, a first (5'→3') RNA oligonucleotide sequence designated as 3WJa, a second (5'→3') RNA oligonucleotide sequence designated as 3WJb, and a third (5'→3') RNA oligonucleotide sequence designated as 3WJc, are combined and base pair to form the trifurcate pRNA 3WJ, wherein a first branch of the 3WJ domain is formed from a 5' portion of the 3WJa sequence and a 3' portion of the 3WJc sequence, a second branch of the 3WJ domain is formed from a 3' portion of the 3WJa sequence and a 5' portion of the 3WJb sequence, and a third branch of the 3WJ domain is formed from a 3' portion of the 3WJb sequence and a 5' portion of the 3WJc sequence, wherein each of said first, second, and third branches comprises a helical region having a plurality of RNA nucleotide pairs that form canonical Watson-Crick bonds. One, two and/or three of the branches of the 3WJs of the present disclosure may also include non-Watson-Crick nucleotide pairs, such as, but not limited to, G-U.

In certain non-limiting embodiments, each of the 3WJa, 3WJb, and 3WJc oligonucleotide sequences of the pRNA 3WJ scaffolds of the present disclosure may comprise, independently, from 8 to 36 nucleotides (e.g., 8, 9, 10, 11, 12, 13, 14, 15, 16, 17, 18, 19, 20, 21, 22, 23, 24, 25, 26, 27, 28, 29, 30, 31, 32, 33, 34, 35, or 36 nucleotides) not including RNA linkers or RNA portions of biologically-active moieties conjugated to the pRNA 3WJ scaffold.

Throughout this disclosure, in reference to mutant constructs, subscripts which include "Δ" represent nucleotide positions of the corresponding wild type pRNA which have been deleted in the mutant. The term "domain" may be used in place of "construct." The term "downstream" when used in reference to an oligonucleotide sequence refers to a direction toward the 3' end of the sequence, and "upstream" refers to a direction toward the 5' end of the sequence.

Biophysical studies on certain presently disclosed phi29 pRNA 3WJ deletion mutant constructs, M2 pRNA 3WJ deletion mutant constructs, and SF5 pRNA 3WJ deletion mutant constructs revealed their enhanced stability relative to a 3WJ portion (also referred to herein as a "stem") of a wild-type (WT) phi29 pRNA. Thus, the described deletion mutant constructs can be used as more robust alternatives to current technologies that utilize the WT phi29 pRNA 3WJ stem as a building block for polyvalent, nanoscale delivery systems. The presently disclosed novel pRNA 3WJ constructs have at least one use as an improved drug delivery scaffold due to their enhanced stability over currently used technologies, such as the previously noted WT phi29 pRNA 3WJ motif. Functional RNAs designed using the enhanced stability phi29 pRNA 3WJ deletion mutants disclosed herein or M2, SF5, or GA1 pRNA 3WJs disclosed herein include but are not limited to: therapeutic delivery vehicles to carry various therapeutic, targeting, or diagnostic molecules, including but not limited to siRNAs, ribozymes, riboswitches, aptamers, and antisense RNA, and linkers for connecting such therapeutic, targeting, or diagnostic molecules, such as but not limited to those shown in U.S. Pat. No. 9,297,013 B2. Complete sequences of wild-type phi29, SF5, M2, and GA1 pRNA are shown in U.S. Pat. No. 8,088,912.

For example, in non-limiting embodiments, an siRNA helix functionally (covalently) attached to the 3WJ scaffold may comprise 10-30, 15-27, or 20-25 nucleotides, and interferes with gene expression through the cleavage of mRNA by a protein/RNA complex named RISC (RNA-induced silencing complex), as also discussed above. The siRNA specifically (e.g., with statistical significance, relative to an appropriate control of irrelevant structure) suppresses the expression of a target protein whose mRNA includes a sequence identical to the sense strand of the siRNA.

In non-limiting embodiments, a ribozyme may comprise an RNA molecule that has enzymatic activity. Ribozymes have significant therapeutic potential and may be capable of regulating gene function by intercepting and cleaving RNA substrates, such as mRNA or the viral genome of RNA containing a sequence complementary to the catalytic center of the ribozyme.

In non-limiting embodiments, an RNA aptamer may be a member of a family of oligonucleotides with functions similar to that of antibodies in their ability specifically to recognize ligands (e.g., organic compounds, nucleotides, or peptides) through the formation of binding pockets. Systematic evolution of ligands by exponential enrichment (SELEX) is a method used to screen for aptamers having desired binding specificities, from randomized RNA pools developed in vitro. Using this technique, various aptamers can be selected for targeting markers relevant to diseases.

In non-limiting embodiments, riboswitches may include RNA components that bind small molecules and control gene expression. As a biological control mechanism, riboswitches can recognize metabolites, induce premature termination of mRNA transcription, block ribosomes from translating mRNAs, cleave mRNAs, and even trigger mRNA destruction.

In non-limiting embodiments, such RNA moieties including siRNAs, ribozymes, antisense RNAs, aptamers, and riboswitches, as well as other catalytic or editing RNAs can, according to art-accepted methodologies, be readily fused to or conjugated with the 3WJ scaffolds to provide a modular system for the assembly of RNA nanoparticles. Among the advantages of the compounds, compositions and methods as disclosed herein, e.g., for RNA nanomedicine, there are included the attributes of self-assembly, high physicochemical and physiological stability, multi-valency, targeted delivery, protein-free (including advantages associated with being non-immunogenic, non-inflammatory, non-toxic, non-eliciting of lymphokine, chemokine or cytokine responses such as an interferon response), nanoscale size, controlled synthesis with defined structure and stoichiometry, combining therapy and detection of therapy effects into one particle.

In non-limiting embodiments, each branch of the 3WJ scaffold may be separately functionalized to carry different therapeutic payloads, reporters and/or targeting ligands thereby forming a multivalent compound. Targeted compounds enable cell-type-specific delivery resulting in a lower concentration of the drug to be administered, thus reducing the side effects. The multivalent approach permits certain embodiments to comprise a mixture of therapeutic agents (e.g., different drugs delivered via a different subunit that may be assembled into the 3WJ nanoparticle complexes assembled herein) thereby producing a synergistic effect. The multi-valency offers an additional advantage in these and/or other contemplated embodiments that permit therapy along with detection of therapeutic effects, combined into one nanoparticle that is introduced in a single administration.

In non-limiting embodiments, RNA nanoparticles comprising the presently disclosed 3WJ scaffolds may be typically and advantageously sized in the nanometer-scale. In non-limiting embodiments, particles ranging from 10-50 nm are suitable as they are large enough to be retained by the body yet small enough to pass through the cell membrane via the cell surface receptor mediated endocytosis. The herein described nanoparticle delivery thus improves the pharmacokinetics, pharmacodynamics, biodistribution, and safety of therapeutic and/or diagnostic agents. Additionally, the protein-free nature of the presently disclosed therapeutic compounds result in these nanoparticles being substantially non-immunogenic; by avoiding the induction of antibodies in a recipient, these embodiments permit safely the repeated administration of the nanoparticles for the treatment of chronic diseases including cancers, viral infections, and genetic ailments.

In non-limiting embodiments, two or three or even more RNA nanostructure domains (e.g., similar or dissimilar domains such as biologically active moiety-containing or other functional domains, for instance, siRNA, molecular targeting moieties, ribozymes, anti-sense RNA, and aptamers) may be covalently connected to the presently disclosed 3WJ scaffolds.

EXPERIMENTAL

Materials and Methods
pRNA 3WJ Construct Design

Figure 1A:
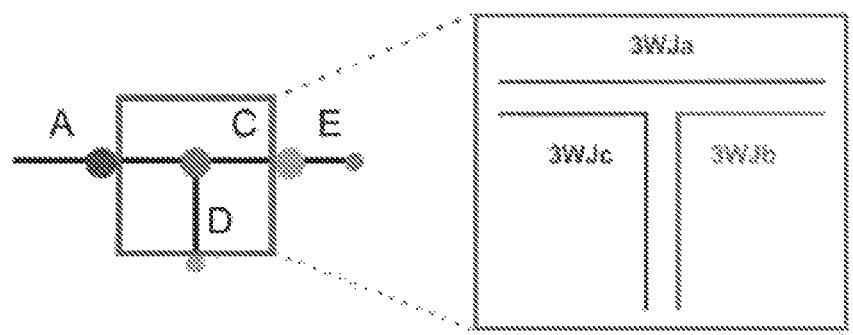
FIG. 1A depicts a ball-and-stick model of prohead or packaging RNA (pRNA), where balls represent loops and sticks represent helices. The central three-way junction (3WJ) portion, which doesn't include the A, CE, and D bulges, is represented within the box. The 3WJ can be assembled from three single RNA oligonucleotide strands (denoted 3WJa, 3WJb, and 3WJc) mixed in approximately equimolar concentrations. The pRNA 3WJ nanomotif, inset, comprises strands 3WJa, 3WJb, and 3WJc which base pair according to Watson-Crick base pairing, except for certain unpaired nucleotides.
Figure 1B:
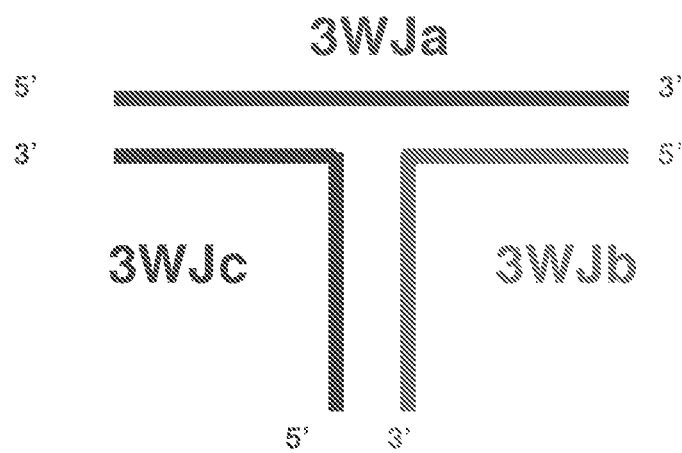
FIG. 1B indicates the 5'-3' direction of each 3WJa, 3WJb, and 3WJc oligonucleotide strand when base paired as the 3WJ construct.

The pRNA 3WJ can be assembled from three RNA oligomers mixed in approximately equimolar concentrations. The pRNA constructs investigated in this study were assembled from three RNA strands designated 3WJa, 3WJb, and 3WJc (FIG. 1A-B). Constructs were designed to encompass the central 3WJ region of folded pRNA, not including the A, CE, and D bulges (FIG. 1A), to form three helices of approximately equal free energies. The pRNA 3WJ constructs utilized herein retained substantial sequence identity to the wild types at the 3WJ "core", and included changes distal to the 3WJ "core" in certain constructs (e.g., FIGS. 2-3) to ensure that the free energy of helix formation for each branch was within 0.1 kcal/mol. The three oligonucleotide sequences for each 3WJ construct are shown in Table 1. The predicted free energy for each branch duplex includes a helix initiation term that assumes two strands come together independently. This is an overestimation of the penalty of helix formation in the third branch formed because this branch should not have the same entropic penalty in the 3WJ. Thus, the calculated 3WJ free energies shown below (e.g., Table 2) actually underestimate the stabilities of the 3WJs. Oligonucleotides were purchased from Integrated DNA Technologies (IDT) and prepared according to the manufacturer's instructions. Purity was confirmed to be >95% by $^{32}$P labeling and gel electrophoresis.

TABLE 1

Figure 5A:
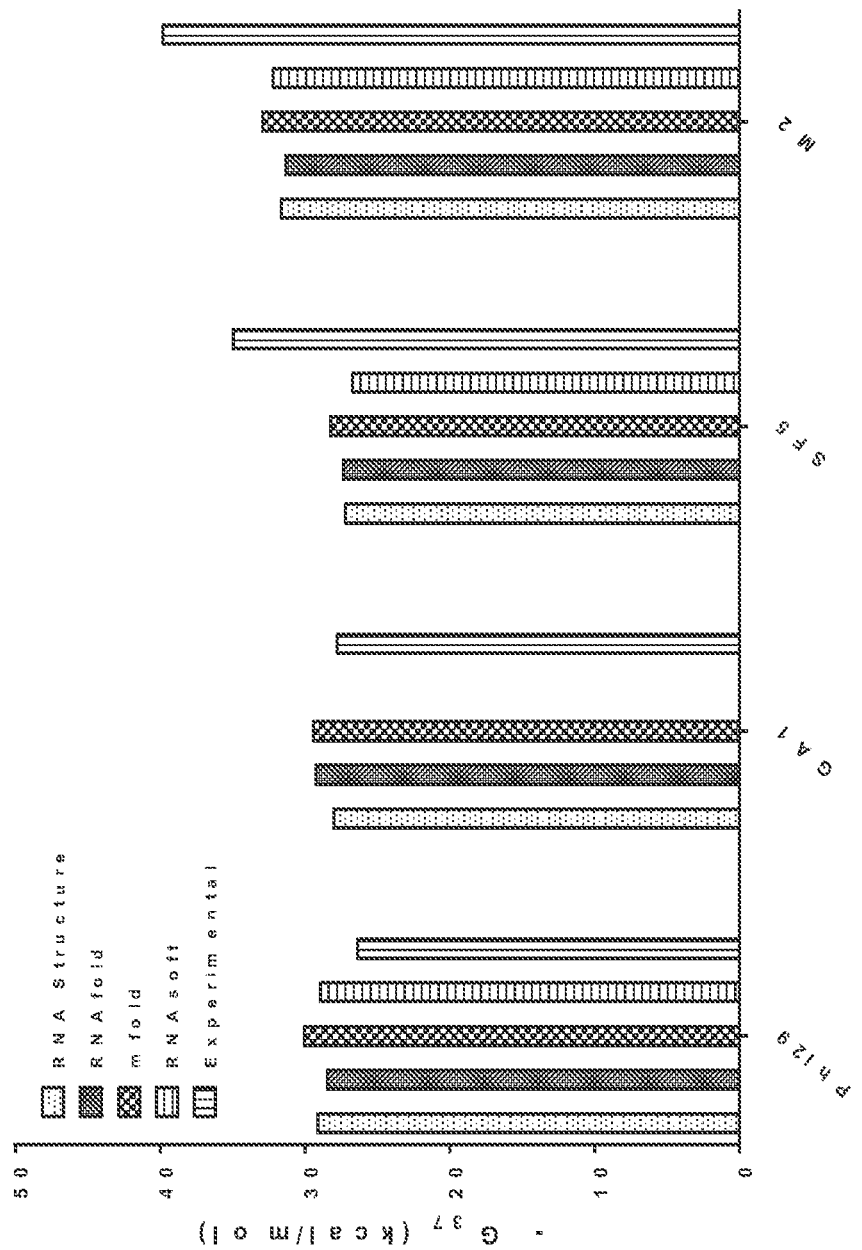
FIG. 5A shows predicted thermodynamic stabilities for various pRNA 3WJ constructs (stem phi29, GA1, SF5, M2) using RNA Structure, RNAfold, mfold, and RNAsoft, and as measured experimentally. Greater $-\Delta G$ indicates greater stability. *RNAsoft did not output a secondary structure free energy for the GA1 pRNA 3WJ due to computer run-time limitations.
Figure 6A:
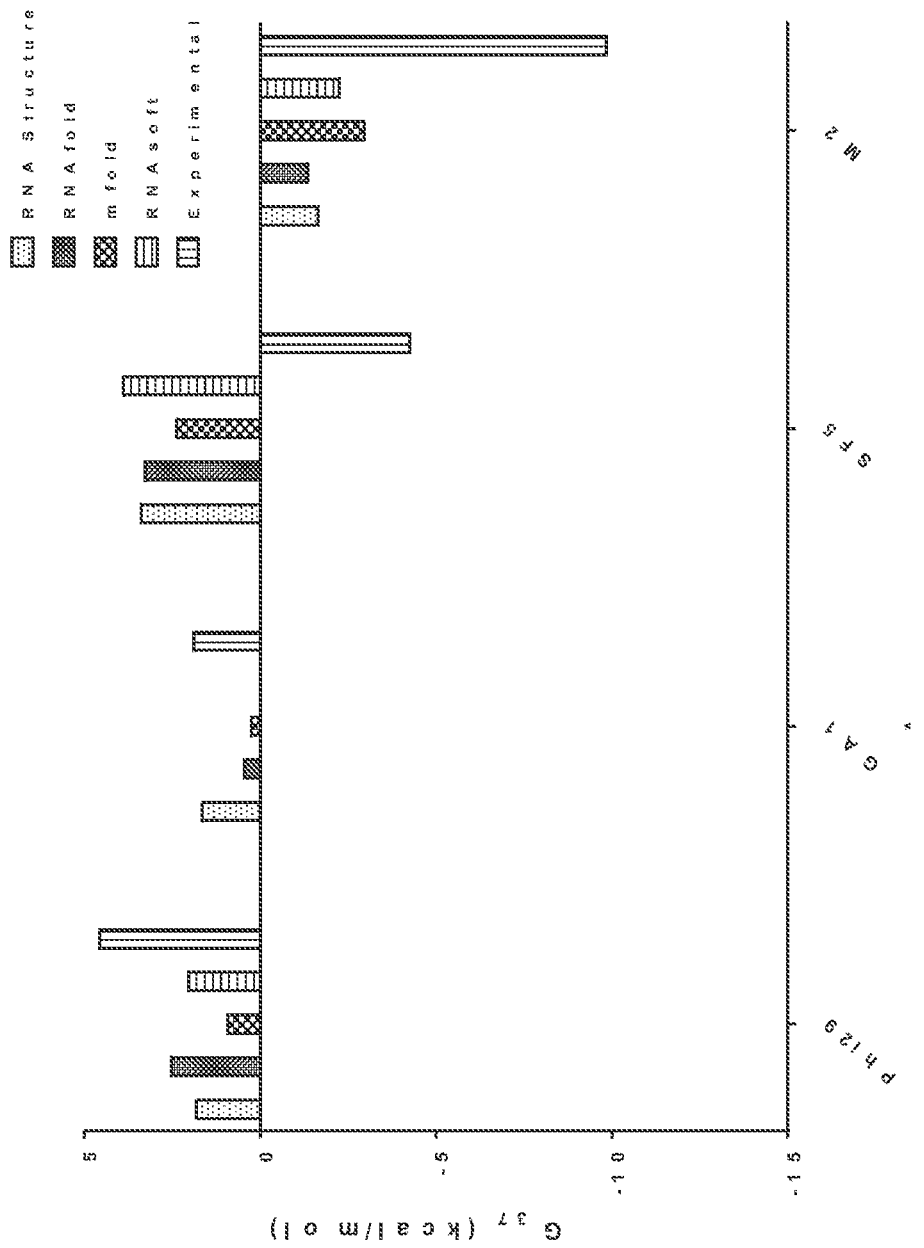
FIG. 6A compares predicted and experimentally measured thermodynamic stabilities for various pRNA 3WJs (phi29, GA1, SF5, M2) using the programs of FIGS. 5A-5B. Greater $-\Delta G$ indicates greater stability. *RNAsoft did not output a secondary structure free energy for the GA1 pRNA 3WJ due to computer run-time limitations.
Figure 6B:
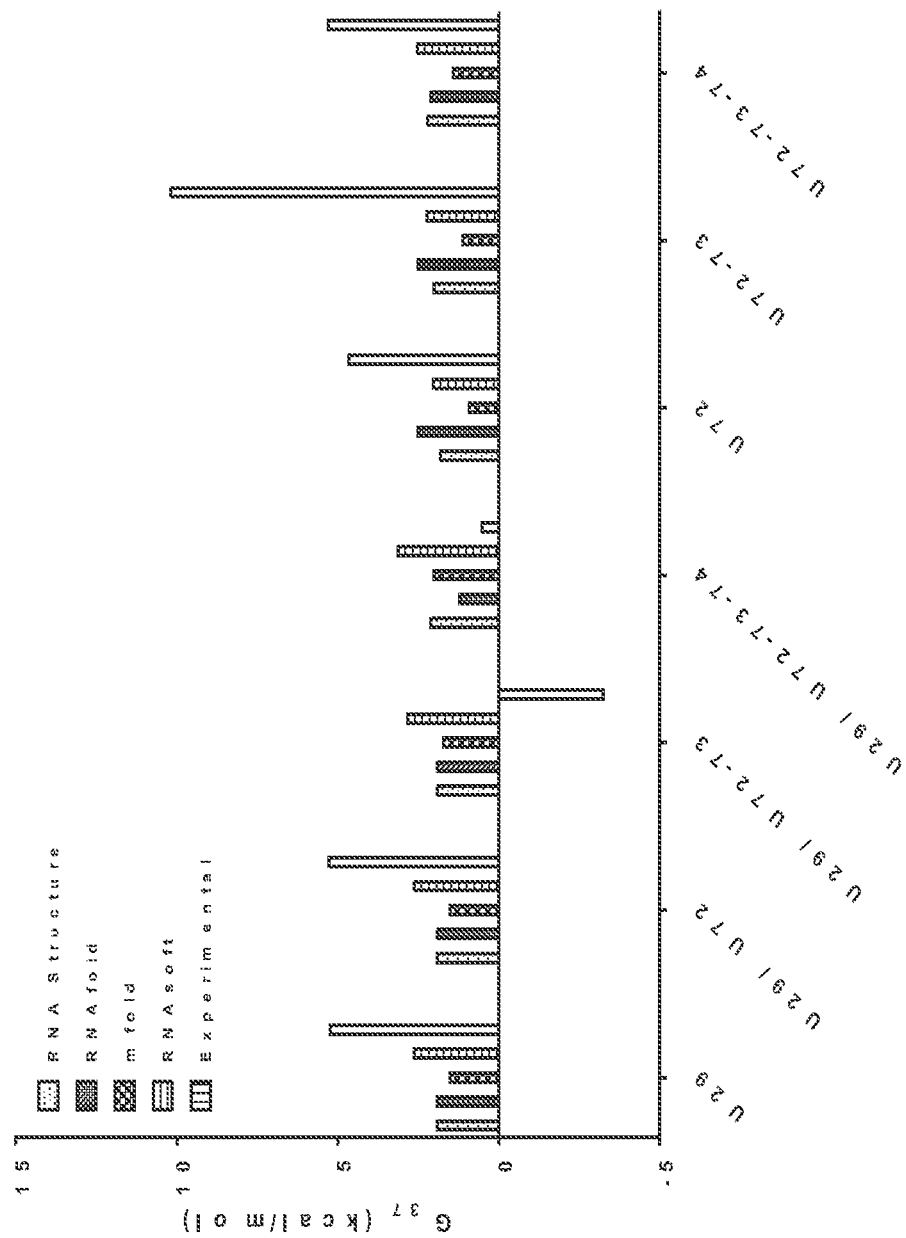
FIG. 6B compares predicted and experimentally measured thermodynamic stabilities for various phi29 pRNA mutant 3WJs using the programs of FIGS. 5A-5B. Greater $-\Delta G$ indicates greater stability.

Component 3WJa, 3WJb, and 3WJc RNA sequences for each pRNA construct tested (FIGS. 5A, 6A, and 6B). Bulge nucleotides which are unpaired in the 3WJ constructs are underlined. Subscripts represent nucleotide positions of the corresponding wilde type pRNA which have been deleted in the mutant.

| Construct | Sequence | SEQ ID NO: |
|---|---|---|
| phi29 | | |
| 3WJa | 5'-CUUGUCAUGUGUAUGUUGCC-3' | 1 |
| 3WJb | 5'-GGCACAUACUUUGUUGAUAGG-3' | 2 |
| 3WJc | 5'-CCUGUCAAUCAUGGCAAG-3' | 3 |
| GA1 | | |
| 3WJa | 5'-CGAUAUAUAGGCUGUGCAAGAUU-3' | 4 |
| 3WJb | 5'-AAUCUUGACAGGUUGUUGGC-3' | 5 |
| 3WJc | 5'-GCUAGCAAUACUAUAUAUCG-3' | 6 |
| SF5 | | |
| 3WJa | 5'-GCUAAUGUAUGUGUGUCCG-3' | 7 |
| 3WJb | 5'-CGGACAGCAGGGGAGCGUGC-3' | 8 |
| 3WJc | 5'-GCACACUCUUGCAUUAGC-3' | 9 |
| M2 | | |
| 3WJa | 5'-GCAAUAGUAUGGCACAUGUGC-3' | 10 |
| 3WJb | 5'-GCACAUGUCACGGGGUAGG-3' | 11 |
| 3WJc | 5'-CCUACCCUCUUACUAUUGC-3' | 12 |
| phi29$_{\Delta U29}$ | | |
| 3WJa | 5'-CUUGUCAUGGUAUGUUGCC-3' | 13 |
| 3WJb | 5'-GGCACAUACUUUGUUGAUAGG-3' | 2 |
| 3WJc | 5'-CCUGUCAAUCAUGGCAAG-3' | 3 |
| phi29$_{\Delta U29/\Delta U72}$ | | |
| 3WJa | 5'-CUUGUCAUGGUAUGUUGCC-3' | 13 |
| 3WJb | 5'-GGCACAUACUUGUUGAUAGG-3' | 14 |
| 3WJc | 5'-CCUGUCAAUCAUGGCAAG-3' | 3 |
| phi29$_{\Delta U29/\Delta U72-73}$ | | |
| 3WJa | 5'-CUUGUCAUGGUAUGUUGCC-3' | 13 |
| 3WJb | 5'-GGCACAUACUGUUGAUAGG-3' | 15 |
| 3WJc | 5'-CCUGUCAAUCAUGGCAAG-3' | 3 |
| phi29$_{\Delta U29/\Delta U72-73-74}$ | | |
| 3WJa | 5'-CUUGUCAUGGUAUGUUGCC-3' | 13 |
| 3WJb | 5'-GGCACAUACGUUGAUAGG-3' | 16 |
| 3WJc | 5'-CCUGUCAAUCAUGGCAAG-3' | 3 |
| phi29$_{\Delta U72}$ | | |
| 3WJa | 5'-CUUGUCAUGUGUAUGUUGCC-3' | 1 |
| 3WJb | 5'-GGCACAUACUUGUUGAUAGG-3' | 14 |
| 3WJc | 5'-CCUGUCAAUCAUGGCAAG-3' | 3 |

TABLE 1-continued

Component 3WJa, 3WJb, and 3WJc RNA sequences
for each pRNA construct tested (FIGS. 5A,
6A, and 6B). Bulge nucleotides which
are unpaired in the 3WJ constructs are
underlined. Subscripts represent nucleotide
positions of the corresponding wilde type
pRNA which have been deleted in the mutant.

| Construct | Sequence | SEQ ID NO: |
|---|---|---|
| phi29$_{\Delta U72\text{-}73}$ | | |
| 3WJa | 5'-CUUGUCAUGU$\underline{G}$UAUG$\underline{U}$UGCC-3' | 1 |
| 3WJb | 5'-GGCACAUAC$\underline{U}$GUUGAUAGG-3' | 15 |
| 3WJc | 5'-CCUGUCAAUCAUGGCAAG-3' | 3 |
| phi29$_{\Delta U72\text{-}73\text{-}74}$ | | |
| 3WJa | 5'-CUUGUCAUGU$\underline{G}$UAUG$\underline{U}$UGCC-3' | 1 |
| 3WJb | 5'-GGCACAUACGUUGAUAGG-3' | 16 |
| 3WJc | 5'-CCUGUCAAUCAUGGCAAG-3' | 3 |

UV Optical Melting

For each 3WJ construct, the three RNA oligomers 3WJa, 3WJb, and 3WJc were mixed in approximately equimolar concentrations spanning a 100-fold dilution range from 0.4 µM to 40 µM. UV optical melting was performed as described previously (Schroeder and Turner 2009), with variation in the analysis for a three-component RNA system. Briefly, melts were carried out under standard melt buffer conditions (1 M sodium chloride, 10 mM sodium cacodylate, 0.5 mM EDTA, pH 7.0) (Gu et al. 2013) using a Beckman Coulter DU-800 spectrophotometer. Absorbances at 260 and 280 nm were measured as a function of temperature from 4° C. to 90° C., both the largest measurable temperature range and the range for which the midpoint and the constructs' expected $T_m$s were approximately equal. In order to form reproducibly the lowest energy structure, RNA samples were heated to 90° C. and slowly cooled prior to melting or the addition of magnesium. The sodium chloride concentration was reduced by an order of magnitude for melts with 10 mM metal ions, but all other conditions remained the same. Due to the presence of EDTA, the effective $Mg^{2+}$ concentration may have been slightly less than 10 mM. For each construct, optical melts of single RNA strands 3WJa, 3WJb, and 3WJc and all pairwise combinations were also performed. Melt curves were fit using Meltwin in order to determine melting temperatures, and thermodynamic parameters were determined from van't Hoff plots where the equilibrium constant $K_{eq}$ was given by Eq. 1:

$$K_{eq} = \frac{1}{(C_T/2n)^{n-1}} \quad \text{(Eq. 1)}$$

where $C_T$=total strand concentration and n=3 for a trimolecular dissociation reaction with equilibria involving non-self-complementary sequences, and where goodness of linear fit, a good estimate of error, was ≥0.90. The sharpness of the melting transition and the linearity of the van't Hoff plots suggest two-state melting; however, the assumption of $\Delta C_p$=0 is not rigorously followed. Although the enthalpies show some temperature dependence, there is a large range of error in the enthalpy and heat capacity values. The errors in enthalpy and entropy are correlated, and thus, the free energy still provides a useful, predictive value. Furthermore, corrections for temperature-dependent changes in heat capacity have a small effect within error of the value for the final free energy of the multibranch loop motif, i.e., <0.5 kcal/mol. Thermodynamic stabilities of the pRNA 3WJ nanomotifs were calculated by subtracting the stability contributions of the RNA helices as calculated from the Nearest Neighbor Database (Table 2, FIGS. 6A-6B).

pRNA 3WJ Secondary Structure and Free Energy Predictions

The secondary structure and stability of each pRNA construct was predicted using four RNA secondary structure prediction programs: RNA Structure, RNAfold, mfold, and RNAsoft. For predictions in RNA Structure, RNAfold, and mfold, pRNA strands 3WJa and 3WJb as well as 3WJb and 3WJc were joined with a 5'-aaaa-3' hairpin and then the construct was folded as a single strand. Free energy predictions were not affected by the position of the hairpins, i.e., whether the hairpins were placed between strands 3WJa and 3WJb and strands 3WJb and 3WJc, between strands 3WJb and 3WJc and strands 3WJc and 3WJa, or between strands 3WJc and 3WJa and strands 3WJa and 3WJb. For predictions in RNAsoft, pRNA strands 3WJa and 3WJb were joined with a 5'-aaaa-3' hairpin and folded with strand 3WJc. Again, free energy predictions were not affected by the position of the hairpin, i.e., whether the hairpin was placed between strands 3WJa and 3WJb, between strands 3WJb and 3WJc, or between strands 3WJc and 3WJa. For each construct, the most stable structure output by each program was the designed structure. No forced base pairs or single strand constraints were used. To correct for the added hairpins, two 5'-aaaa-3' hairpin penalties were subtracted from the secondary structure stabilities output by RNA Structure, RNAfold, and mfold. For stabilities predicted by RNAsoft, one 5'-aaaa-3' hairpin penalty was subtracted. Because the calculations take into account the initiation terms for the 3WJs, their free energies are accurate within error whether in the context of a single-stranded RNA, a duplex, or a three-component system. The entropic penalties for bringing together two oligomers are included in the free energy of initiation terms. The free energies of initiating an RNA hairpin and RNA intermolecular interactions are 5.4±0.2 kcal/mol to 6.4±0.2 kcal/mol (spanning loop lengths n=3 to n=9) and 4.09±0.2 kcal/mol, respectively. Thus, while there is a substantial entropic energy difference in bringing together three oligonucleotide strands compared to a single strand self-folding, the calculation of the free energy of the multibranch loop accounts for this difference and makes comparison of the 3WJ motif comparable in different contexts.

Electrophoretic Gel Mobility Shift Assays

Formation of the pRNA 3WJ constructs was monitored using electrophoretic gel mobility shift assays (EMSAs). RNA at a concentration of 40 µM in standard melt buffer (1 M sodium chloride, 10 mM sodium cacodylate, 0.5 mM EDTA, pH 7.0) was heated to 80° C. for 10 s and then cooled to 4° C. at a rate of 0.1° C./s in an MJ Research PTC-200 Peltier Thermal Cycler. The RNA was mixed with sucrose loading dye and run in TAE buffer at 50V and 4° C. in pre-cooled, 2% (w/v) agarose stained with ethidium bromide. Mobility of a single RNA strand (phi29 3WJa), a pairwise combination (phi29 3WJa+3WJb), and all assembled pRNA 3WJs were monitored.

Results pRNA 3WJ Nanomotif Stabilities

Thermodynamic parameters determined by UV optical melting for each construct and its respective 3WJ nanomotif are reported in Table 2. The GA1, SF5, and M2 pRNA 3WJs showed greater stability than the stem phi29 pRNA 3WJ (Table 2).

TABLE 2

Thermodynamic parameters for pRNA 3WJ constructs and nanomotifs. Errors in enthalpy, entropy, and free energy are estimated to be 10%, 10%, and 5%, respectively.

| Construct | $\Delta H$ (kcal mol$^{-1}$) | $\Delta S$ (cal mol$^{-1}$ K$^{-1}$) | $\Delta G_{37}$ (kcal mol$^{-1}$) | $\Delta G_{37}$ 3WJ (kcal mol$^{-1}$) |
|---|---|---|---|---|
| phi29 | −230.8 | −658.7 | −26.5 | 4.6 |
| GA1 | −317.9 | −935.0 | −27.9 | 1.9 |
| SF5 | −336.1 | −970.7 | −35.0 | −4.3 |
| M2 | −350.7 | −1002.1 | −39.9 | −9.9 |
| phi29$_{\Delta U29}$ | −215.6 | −611.9 | −25.8 | 5.3 |
| phi29$_{\Delta U29/\Delta U72}$ | −201.6 | −566.8 | −25.8 | 5.3 |
| phi29$_{\Delta U29/\Delta U72-73}$ | −302.3 | −863.8 | −34.4 | −3.3 |
| phi29$_{\Delta U29/\Delta U72-73-74}$ | −291.6 | −841.7 | −30.5 | 0.6 |
| phi29$_{\Delta U72}$ | −225.4 | −641.5 | −26.4 | 4.7 |
| phi29$_{\Delta U72-73}$ | −124.2 | −333.1 | −20.9 | 10.2 |
| phi29$_{\Delta U72-73-74}$ | −209.5 | −592.3 | −25.8 | 5.3 |

Figure 4A:
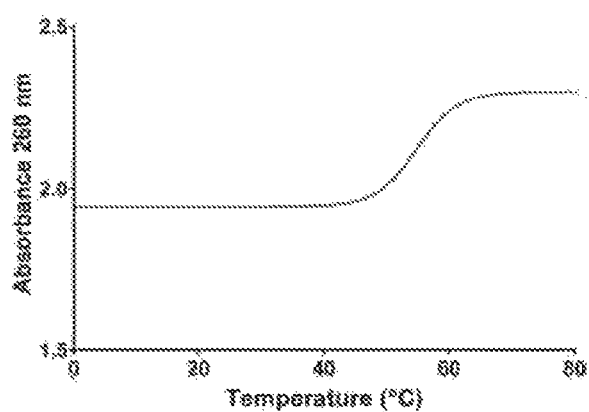
FIG. 4A shows a nonlinear melt curve fit ($R^2>0.99$) for the phi29 3WJ construct of FIG. 2 collected at 31.2 µM showing a sharp, cooperative transition. Data points were collected at a rate of 6/s with a heating rate of 1° C./min.
Figure 4B:
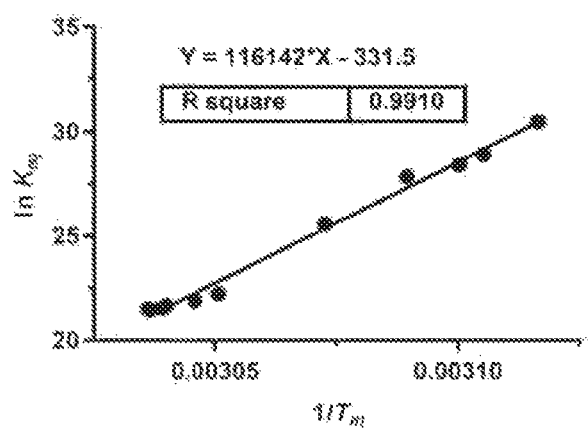
FIG. 4B is a graph of a van't Hoff plot of phi29 3WJ melt data ($R^2>0.99$), where the slope is $-\Delta H/R$ and the y-intercept is $\Delta S/R$. Data were fit using the Marquardt-Levenberg method in Meltwin.

Melt curves showed very sharp transitions, supporting the assumption of a cooperative transition from the RNA triplex to single-stranded RNAs (FIG. 4A). None of the single strand or pairwise combination melts showed a significant transition that would compete with the 3WJ (data not shown). For example, a melt of phi29 strands 3WJa and 3WJb showed a transition with a melting temperature of 51° C., while the complete 3WJ (i.e., strands 3WJa, 3WJb, and 3WJc together) showed a transition with a melting temperature of 56° C. However, formation of the 3WJ is favored when all three strands are present. As previously shown for non-self-complementary RNA duplexes, the non-self-complementary duplex will form even when the $T_m$ for an alternative conformation of a single strand forming a self-complementary duplex has a higher $T_m$ if the enthalpy is more favorable for the non-self-complementary duplex. Free energies for the 3WJ constructs were calculated from van't Hoff plots, where the goodness of linear fit was ≥0.90 for all melts (FIG. 4B). Thermodynamic stabilities of the pRNA 3WJ nanomotifs were calculated by subtracting the stability contributions of the RNA helices as calculated from the Nearest Neighbor Database (Table 2, FIGS. 6A-6B). The free energies for the investigated 3WJs range from −9.9 kcal/mol to 10.2 kcal/mol (Table 2). By comparison, 1.4 kcal/mol at 37° C. is approximately one order of magnitude in a binding constant. Thus, the range of free energies of formation for the investigated 3WJs spans 14 orders of magnitude in terms of binding constants.

The phi29 pRNA 3WJ is stabilized when certain uridine (U) residues are deleted from the junction. Specifically, the following two deletion combinations increased stability relative to the WT phi29 pRNA 3WJ: (1) deletion of a single U bulge (U29) in strand 3WJa along with two of the three U residues in the tri-U bulge in strand 3WJb (i.e., U72-73-74); and (2) deletion of all bulge U residues at the 3WJ (i.e., U29/U72-73-74) (Table 2, FIG. 2). Other investigated deletions either did not significantly affect the stability of the phi29 pRNA 3WJ or actively destabilized it (Table 2).

Figure 5B:
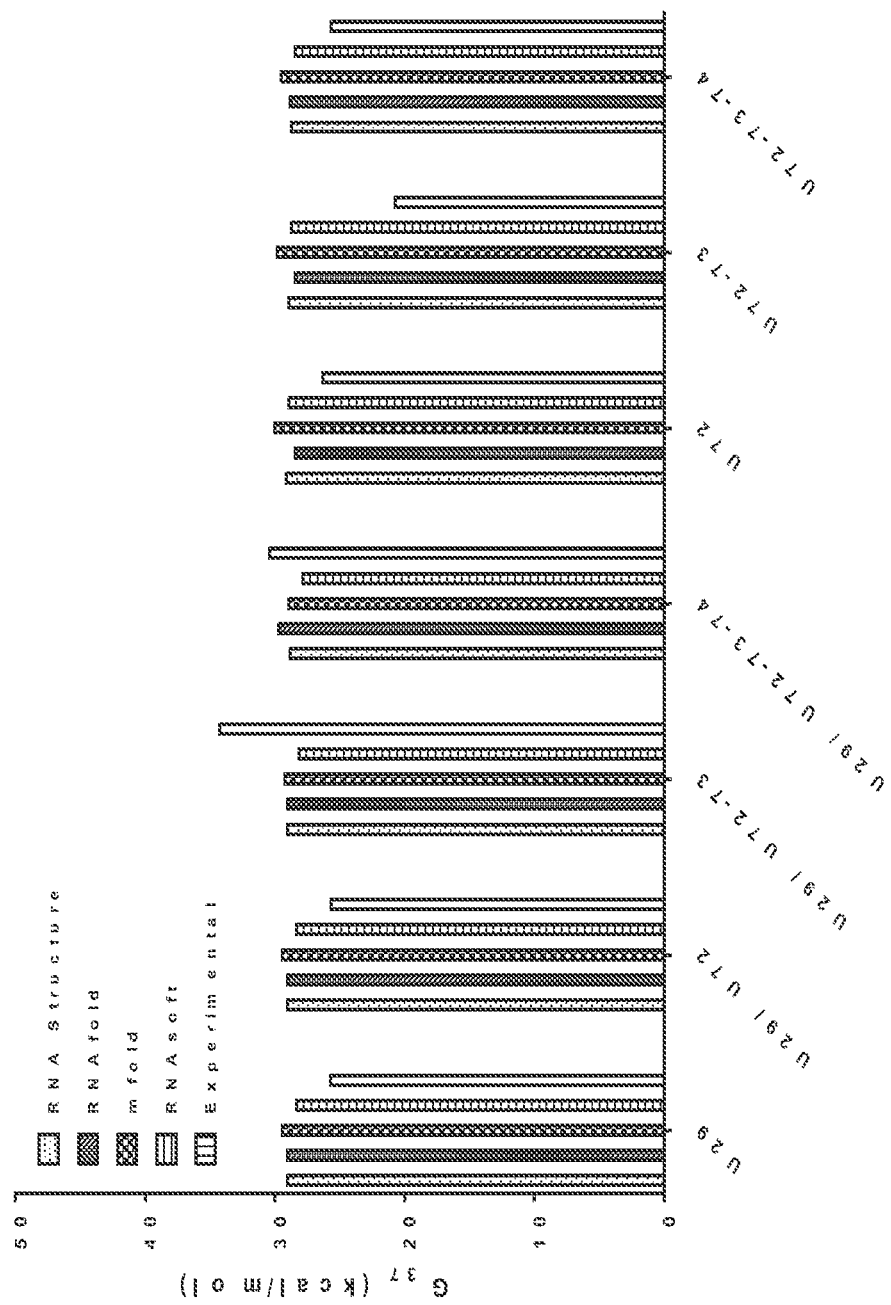
FIG. 5B shows predicted thermodynamic stabilities for various phi29 pRNA 3WJ mutant constructs using RNA Structure, RNAfold, mfold, and RNAsoft, and as measured experimentally. Greater $-\Delta G$ indicates greater stability.

Of the four RNA secondary structure prediction programs used, none accurately predicted either the actual free energies of the junctions or variations in mutant phi29 pRNA 3WJ stabilities (FIGS. 5A-5B). Best predictions ranged from within 1 kcal/mol of the measured free energy (for phi29$_{\Delta U29/\Delta U72-73-74}$, by RNAsoft) to 9 kcal/mol (for phi29$_{\Delta U72-73}$, by RNAfold), while worst predictions ranged from within 1 kcal/mol (for phi29$_{\Delta U29/\Delta U72-73-74}$, by RNAsoft) to 11 kcal/mol (for phi29$_{\Delta U72-73}$, by RNAfold). At best, the prediction programs were off by an average of 4 (±2) kcal/mol from measured free energies.

Metal Ion Binding

Figure 7:
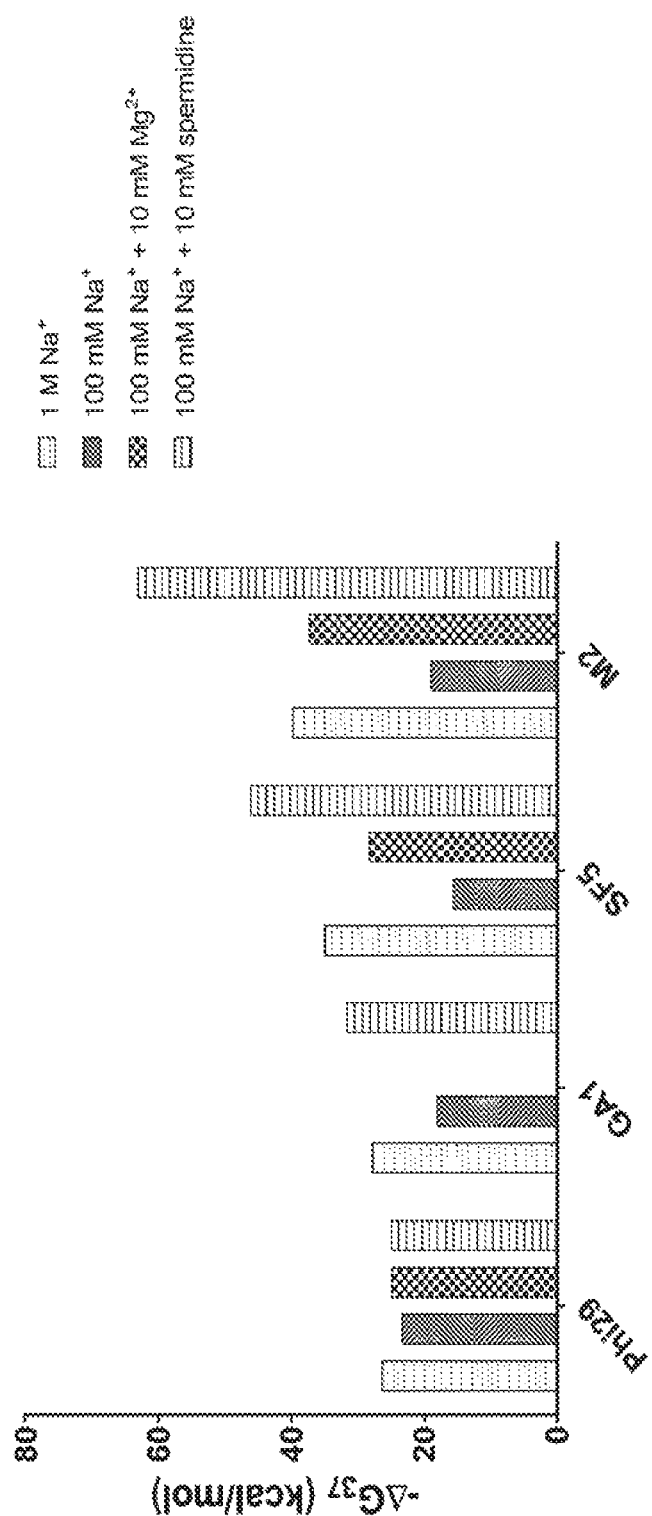
FIG. 7 shows metal ion effects on four pRNA 3WJ constructs. Optical melts of the GA1 3WJ in 100 mM $Na^+$ and 10 mM $Mg^{2+}$ did not meet the van't Hoff plot goodness of linear fit cutoff criterion of $\geq 0.90$.

The effects of Na$^+$, Mg$^{2+}$, and spermidine (a 3$^+$ charged species) on pRNA 3WJ construct stabilities are depicted in FIG. 7. Relative to 100 mM NaCl, the phi29 pRNA 3WJ construct was nearly equally stabilized by Mg$^{2+}$ and spermidine, while the GA1, SF5, and M2 pRNA 3WJ constructs were differentially affected by these ions. Addition of Mg$^{2+}$ stabilized both the SF5 and M2 pRNA 3WJ constructs. The addition of spermidine had an increasing stabilizing effect on the GA1, SF5, and M2 pRNA 3WJ constructs, respectively (FIG. 7).

Electrophoretic Gel Mobility Shift Assays

Figure 8:
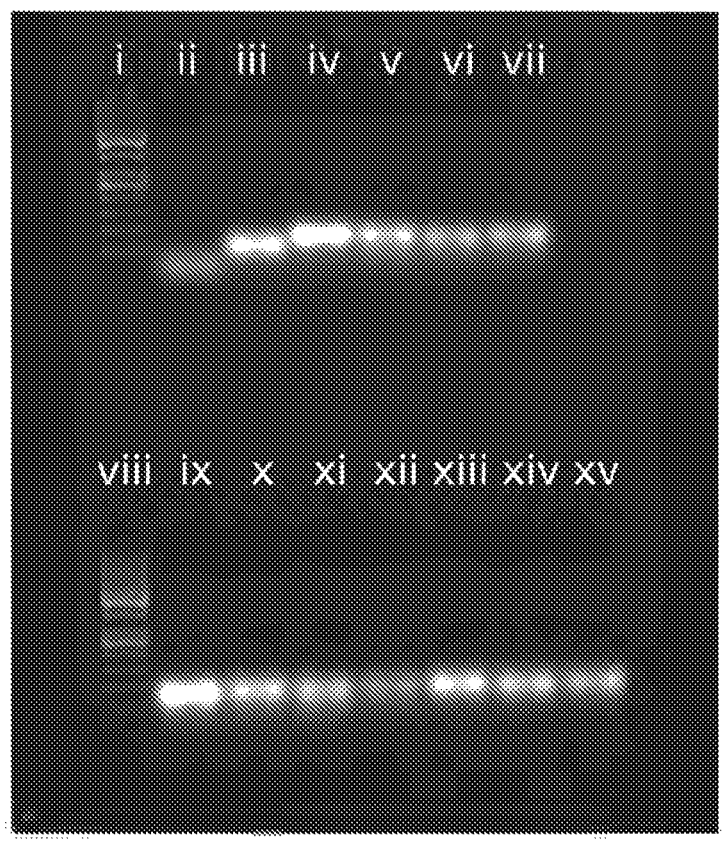
FIG. 8 shows the gel mobility of a 50 bp ladder (Lanes i and viii), phi29 strand 3WJa (Lane ii), phi29 strands 3WJa+3WJb (Lane iii), phi29 3WJ construct (Lane iv), GA1 3WJ construct (Lane v), SF5 3WJ construct (Lane vi), M2 3WJ construct (Lane vii), $phi29_{\Delta U29}$ construct (Lane ix), $phi29_{\Delta U29/\Delta U72}$ construct (Lane x), $phi29_{\Delta U29/\Delta U72-73}$ construct (Lane xi), $phi29_{\Delta U29/\Delta U72-73-74}$ construct (Lane xii), $phi29_{\Delta U72}$ construct (Lane $phi29_{\Delta U72-73}$ construct (Lane xiv), and $phi29_{\Delta U72-73-74}$ construct (Lane xv). Assembly was performed in standard melt buffer (1 M sodium chloride, 10 mM sodium cacodylate, 0.5 mM EDTA, pH 7) to confirm formation of the 3WJ constructs under optical melting conditions. Phi29 strand 3WJa (Lane ii) and strands 3WJa+3WJb (Lane iii) were included as references. All 3WJ constructs run at approximately the same rate.

A gel depicting the mobility of all pRNA 3WJ constructs under standard melt buffer conditions (1 M sodium chloride, 10 mM sodium cacodylate, 0.5 mM EDTA, pH 7.0) relative to a single strand (phi29 3WJa) and a pairwise combination (phi29 3WJa+3WJb) is shown in FIG. 8. All 3WJ constructs run at approximately the same rate. Additionally, gels depicting the mobility of each pRNA 3WJ construct relative to each single RNA strand and all pairwise combinations in TMS buffer (50 mM Tris-HCl, pH 7.8, 100 mM NaCl, 10 mM MgCl$_2$) were compared to previous work published on the assembly and stabilities of various biological RNAs (data not shown). For each gel, mobility decreased as more components of the RNA system were added, indicating formation of a higher molecular weight complex. Single strands showed the fastest migration and pairwise combinations showed intermediate migration relative to a slow-migrating band that appeared when all three RNA 3WJ strands were present (FIG. 8), indicating that the three RNA components interact more favorably than any two components, and confirming formation of the pRNA 3WJ from strands 3WJa, 3WJb, and 3WJc.

Figure 9A:
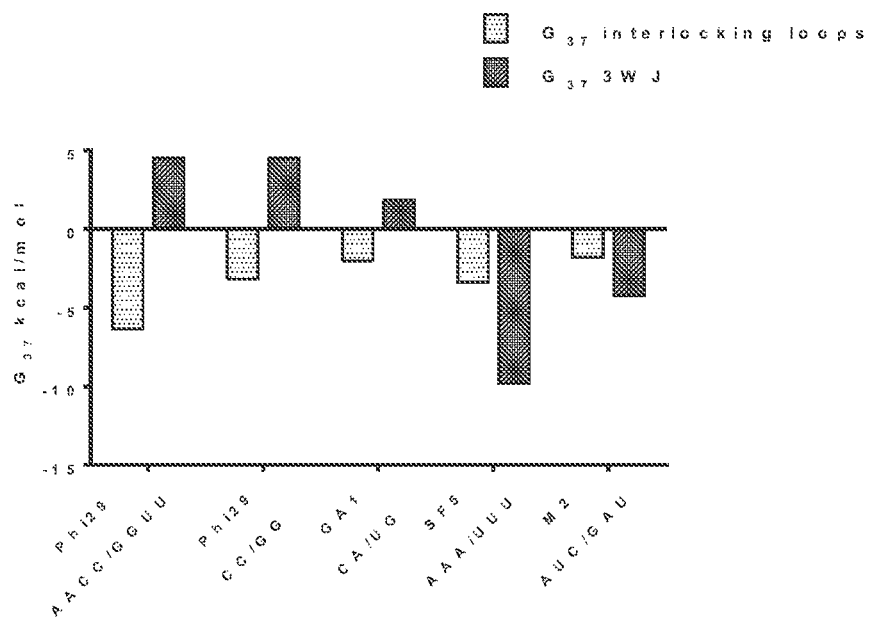
FIG. 9 shows experimental 3WJ data presented with interlocking loop stabilities calculated using the Nearest Neighbor Database of sequences reported by (A) Gu and Schroeder (Gu X, Schroeder S. 2011. Different sequences show similar quaternary interaction stabilities in prohead viral RNA self-assembly. *Journal of Biological Chemistry* 286: 14419-14426). and (B) Hao and Kieft (Hao Y, Kieft J S. 2014. Diverse self-association properties within a family of phage packaging RNAs. RNA 20: 1-16). Interlocking loop sequences are provided for each pRNA. Both the experimental stability data and the calculated stability data were determined for RNA in 1 M sodium chloride.
Figure 9B:
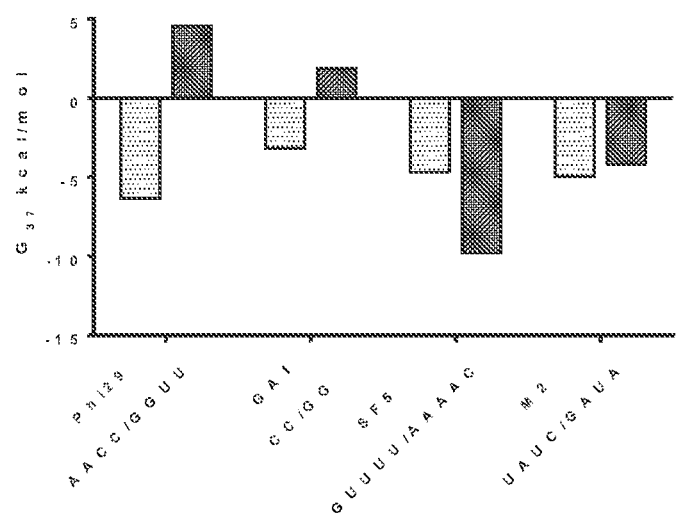

3WJ Stabilities in Relation to Loop-Loop Interaction Stabilities and Self-Assembly Among the investigated pRNA 3WJ constructs, the SF5 and M2 pRNA 3WJs were most thermodynamically stable, making them attractive alternatives to the stem phi29 pRNA 3WJ scaffold used in pRNA-based nanotechnology. Interestingly, these pRNAs also have shown the highest propensity for self-assembly under the laboratory conditions studied thus far. Analyses of our measured 3WJ stabilities with loop-loop interaction stabilities calculated from sequences provided by Gu and Schroeder (Gu and Schroeder 2011, op.cit.) and Hao and Kieft (Hao and Kieft 2014, op.cit.) provide insights into whether the 3WJ nanomotif plays a compensatory role in stabilizing pRNA. The analyses indicated that while loop-loop interactions are all favorable, 3WJs have a wider range of stabilities (FIG. 9A-B). Specifically, the phi29 and GA1 pRNAs have less favorable 3WJ stabilities, while the M2 and SF5 pRNAs have more favorable 3WJ stabilities (FIG. 9A-B). For phi29 and GA1 pRNAs, the loop-loop interaction stabilities are offset by 3WJ stabilities, while for SF5 and M2 pRNAs, the loop-loop interactions and the 3WJ are both stabilizing. The combination of stabilizing nanomotifs may help explain why only SF5 and M2 pRNAs have shown in vitro self-assembly of higher order multimers. Consistent with their increased thermodynamic stabilities and propensities to assemble into higher-order multimers relative to phi29, the SF5 and M2 sequences may both adopt 3WJ pre-organizations that do not require the disruption of existing coaxial stacking or other favorable interactions in order to self-assemble.

Here we show that the ΔU29/ΔU72-73 and ΔU29/ΔU72-73-74 deletions in the phi29 pRNA 3WJ are stabilizing (Table 2), indicating alternatives to stem phi29 pRNA 3WJ scaffolds in the rational design of functional RNAs.

Structure-Energetics Relationships in the pRNA 3WJ

The new thermodynamic data presented here provide a foundation for inferences about RNA structure-energetics relationships, especially for the four bulge U residues at the 3WJ. Non-Watson-Crick base pairing predominates in RNA 3D structure, forming motifs that facilitate RNA-RNA interactions and bind ligands. The phi29 3WJ crystal structure revealed the formation of a cis base pair between the Watson-Crick edges of U29 and U72 as well as base stacking between U29 and U74. By comparison, the phi29 pRNA 3WJ constructs in which U29 and at least one of the three U residues in the tri-U bulge (i.e., U72-73-74) were retained did not appear to have equivalent thermodynamic stabilities, despite the possibility of base pair formation across these constructs' 3WJs. However, the stability of a 3WJ where U29 and two of the three U residues in the tri-U bulge were retained was nearly equal to that of the stem phi29 pRNA 3WJ (4.7 vs. 4.6 kcal/mol, respectively). Interestingly, notable increases in the stability of the phi29 pRNA 3WJ occurred only when one of the U residues in the tri-U bulge was retained (−3.3 kcal/mol), or when all bulge U residues at the 3WJ were deleted (0.6 kcal/mol). Neither of these 3WJs would permit the observed base pairing or base stacking between U residues across the junction, suggesting that pairing and stacking are not the only favorable tertiary interactions stabilizing the junction. These mutations may allow for different, favorable helical coaxial stacking interactions, which may contribute to the stability differences observed.

Free energy outputs by RNA secondary structure prediction programs were not accurately predictive. While all of the programs implemented in this work utilized the same free energy database, the way that multibranch loops are predicted varies in different RNA structure prediction programs. The prediction may consider all possible conformations of coaxial stacking, include only the single most favorable coaxial stacking arrangement, or include knowledge-based parameters from analysis of known secondary structures. None of the algorithms was able to account for the magnitude of differences observed among the measured stabilities of the 3WJs investigated herein. All programs overestimated the stabilities of the phi29 and GA1 pRNA 3WJ constructs and underestimated the stabilities of the SF5 and M2 pRNA 3WJ constructs (FIGS. 5A-6B). Furthermore, none of the programs' predictions discriminated between the stabilities of constructs with deletions in the stem phi29 pRNA 3WJ. For example, neither the mutant that was shown to have the highest stability, nor the mutant that was shown to have the lowest stability, was predicted as such (FIGS. 5A-6B). Instead, deletion mutants were all predicted to have roughly the same free energies (within ~1 kcal/mol).

Prohead RNA (pRNA) is an important component of the phi29-like bacteriophage DNA packaging motor. Due to its stability and self-assembling properties in vitro, pRNA has been used successfully as a scaffold in the rational design of functional RNA supramolecular structures. Prior to the presently disclosed work, the stabilities of pRNA sequences other than phi29 pRNA have been relatively underexplored. The present results demonstrate that certain stem and mutated pRNA 3WJs are more stable than the stem phi29 pRNA 3WJ.

Serum Stability

In results obtained from UV optical melting studies under standard melt buffer conditions, at least five 3WJs were demonstrated to be more thermodynamically stable (i.e., have a more negative $\Delta G_{37}$) relative to the stem phi29 3WJ (FIG. 2), including GA1 3WJ (FIG. 2), SF5 3WJ (FIG. 3), M2 3WJ (FIG. 3), phi29$_{\Delta U29/\Delta U72-73}$ 3WJ (FIG. 12), phi29$_{\Delta U29/\Delta U72-73-74}$ 3WJ (FIG. 13) (Table 2). These constructs, comprising 3WJa, 3WJb, and 3WJc sequences, were therefore demonstrated to be highly stable in comparison to the stem phi29 3WJ construct (FIG. 2) under standard melt buffer conditions. In order to probe the correlation between in vitro stability determined by UV optical melting in standard melt buffer and stability in biological fluids, degradation of the above thermostable pRNA 3WJ constructs was monitored after exposure to human blood serum at physiological temperature. RNA strands 3WJa, 3WJb, and 3WJc were mixed in approximately equimolar concentrations and incubated with human blood serum at 37° C. The 3WJs were recovered using phenol extraction/ethanol precipitation and resuspended in standard melt buffer. Degradation was analyzed using gel electrophoresis under the same conditions as outlined above for EMSAs.

Figure 2:
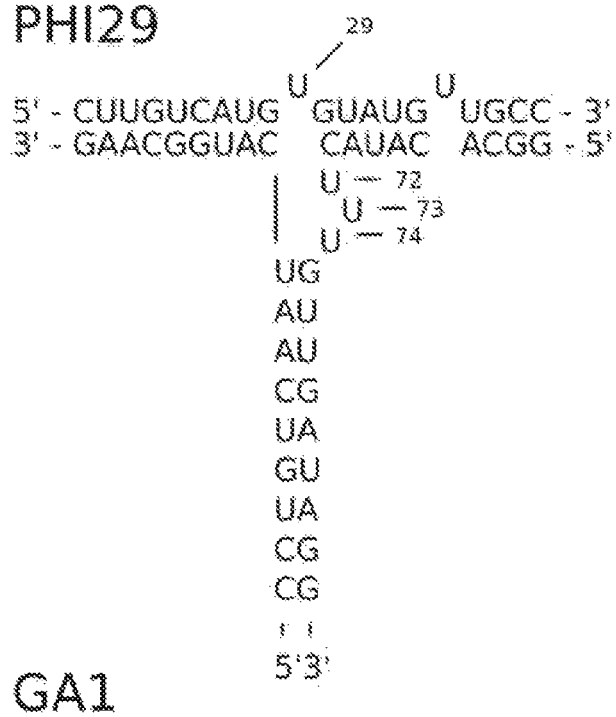
FIG. 2 shows primary and secondary structures of phi29 and GA1 pRNA 3WJ constructs. Nucleotides which do not form Watson-Crick base pairs are indicated as single bases. The phi29 construct comprises SEQ ID NOS:1-3. The GA1 construct comprises SEQ ID NOS:4-6.
Figure 2:
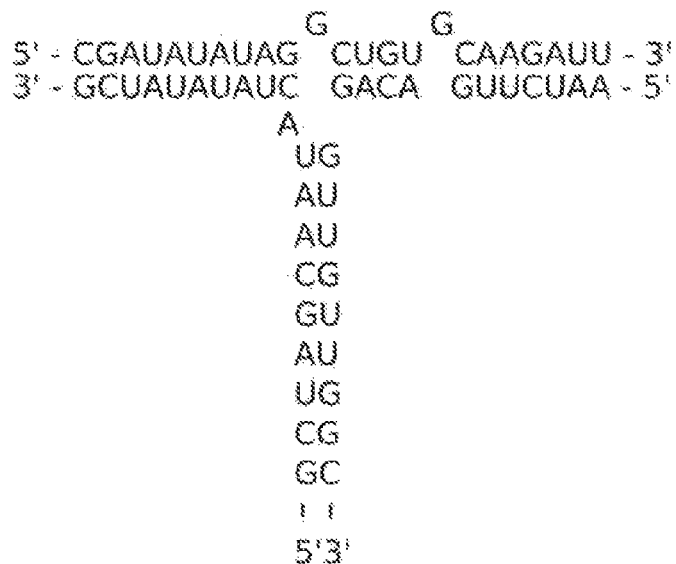
Figure 3:
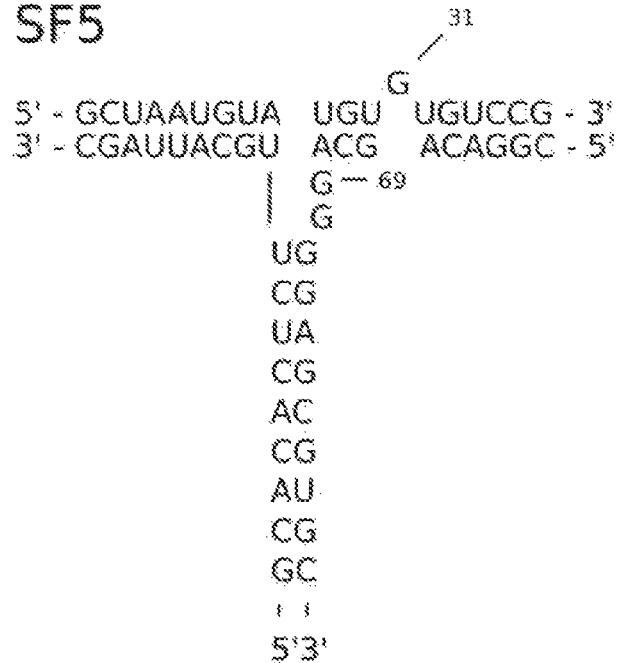
FIG. 3 shows primary and secondary structures of SF5 and M2 pRNA 3WJ constructs. Nucleotides which do not form Watson-Crick base pairs are indicated as single bases. The SF5 construct comprises SEQ ID NOS:7-9. The M2 construct comprises SEQ ID NOS:10-12.
Figure 3:
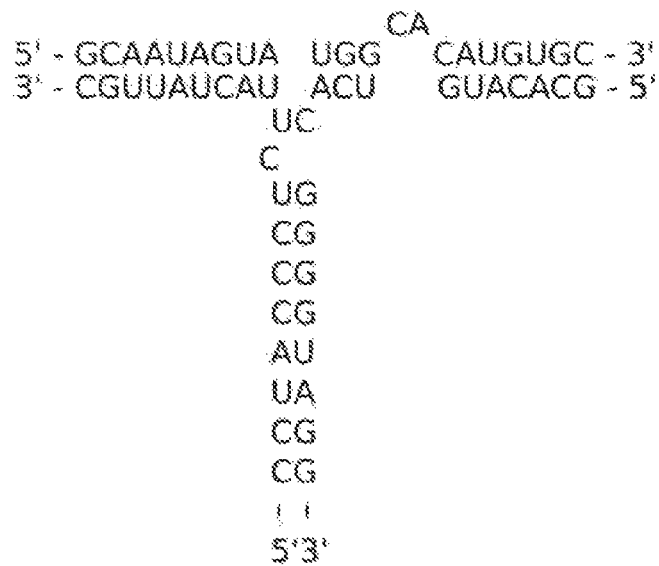
Figure 10A:
FIG. 10A shows gel mobility of 10 µM assembled 3WJ constructs in 2% (w/v) agarose stained with ethidium bromide in TAE buffer following a 10-minute exposure to 100-fold diluted human blood serum. All reactions were carried out at 37° C. Lane (i) 50 bp DNA ladder, (ii) phi29 3WJ construct in standard melt buffer+1 unit RNase T1 (positive degradation control), (iii) phi29 3WJ construct, (iv) GA1 3WJ construct, (v) SF5 3WJ construct, (vi) M2 3WJ construct, (vii) $phi29_{\Delta U29/\Delta U72-73}$ 3 WJ construct, (viii) $phi29_{\Delta U29/\Delta U72-73-74}$ 3 WJ construct.
Figure 10B:
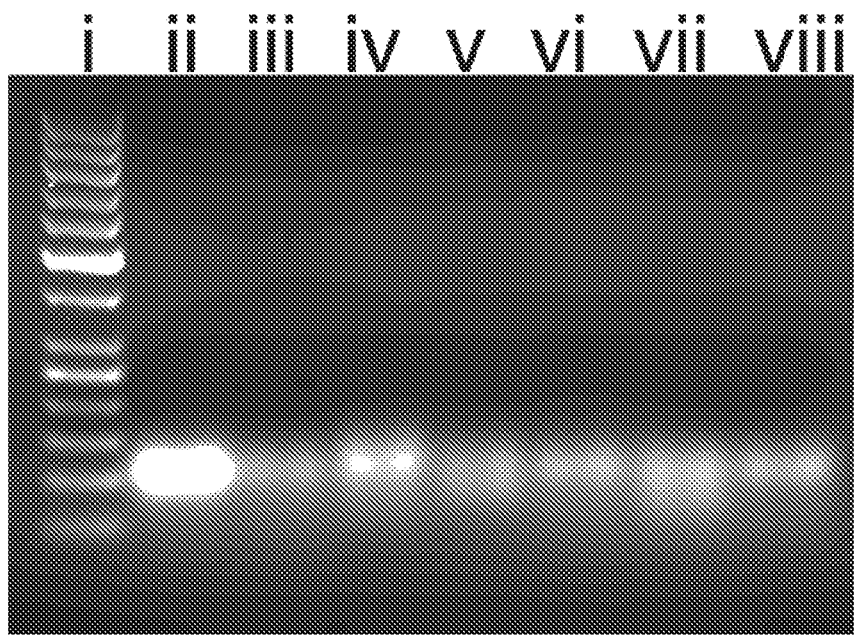
FIG. 10B shows further gel mobility results for 10 µM assembled 3WJ constructs in 2% (w/v) agarose stained with ethidium bromide in TAE buffer following a 10-minute exposure to 100-fold diluted human blood serum from a second blood donor. All reactions were carried out at 37° C.

FIG. 10A shows degradation results for the thermostable 3WJ constructs at 10 µM in 2% (w/v) agarose stained with ethidium bromide in TAE buffer following a 10-minute exposure in 100-fold diluted human blood serum. All reactions were carried out at 37° C. Lane (i) 50 bp DNA ladder, (ii) phi29 3WJ construct in standard melt buffer+1 unit RNase T1 (positive degradation control), (iii) phi29 3WJ construct (FIG. 2), (iv) GA1 3WJ construct (FIG. 2), (v) SF5 3WJ construct (FIG. 3), (vi) M2 3WJ construct (FIG. 3), (vii) phi29$_{\Delta U29/\Delta U72-73}$ 3 WJ construct (FIG. 12A), (viii) phi29$_{\Delta U29/\Delta U72-73-74}$ 3 WJ construct (FIG. 12B). Standard melt buffer was 1 M sodium chloride, 10 mM sodium cacodylate, and 0.5 EDTA, at pH 7. At least two 3WJ constructs showed less degradation and thus were demonstrated to be more stable in human blood serum relative to the stem phi29 3WJ construct (FIG. 2), including, but not limited to, the SF5 3WJ construct (FIG. 3) the and M2 3WJ construct (FIG. 3). These constructs, comprising 3WJa, 3WJb, and 3WJc sequences, were therefore demonstrated to be highly stable in comparison to the stem phi29 3WJ construct (FIG. 2). FIG. 10B shows further degradation results for the previously demonstrated serum-stable 3WJ constructs and mutant SF5 3WJ constructs at 10 µM in 2% (w/v) agarose stained with ethidium bromide in TAE buffer following a 10-minute exposure to 100-fold diluted human blood serum from a second blood donor. All reactions were carried out at 37° C. Lane (i) 50 bp DNA ladder, (ii) phi29 3WJ construct in standard melt buffer (negative degradation control), (iii) phi29 3WJ construct, (iv) M2 3WJ construct, (v) SF5 3WJ construct, (vi) SF5$_{\Delta G31}$ 3 WJ construct, (vii) SF5$_{\Delta G69}$ 3 WJ construct, SF5$_{\Delta G-31/\Delta G-69}$ 3 WJ construct. The mutant SF5 3WJ constructs SF5$_{\Delta G31}$ and SF5$_{\Delta G31/\Delta G69}$ show improved stability in human blood serum relative to the SF5 3WJ construct.

FIGS. 10A-10B compare pRNA 3WJ constructs' stabilities in human blood serum from two different donors. These serum stability assay results indicate that the SF5 and M2 3WJ constructs and SF5$_{\Delta G31}$ and SF5$_{\Delta G31/\Delta G69}$ deletion mutant 3WJ constructs are more stable in human blood serum than the stem phi29 3WJ construct. The SF5 and M2 3WJ constructs also showed greater stability than the GA1 3WJ construct and phi29$_{\Delta U29/\Delta U72-73}$ and phi29$_{\Delta U29/U72-73-74}$ deletion mutant 3WJ constructs.

Further time course analysis was conducted on the stem phi29 3WJ (FIG. 2), SF5 3WJ (FIG. 3), and M2 3WJ (FIG. 3) constructs. Gel mobility results are shown in FIG. 11. 3WJ constructs (10 μM) were analyzed in 2% (w/v) agarose stained with ethidium bromide in TAE buffer following exposure to 1000-fold diluted human blood serum for 10 minutes, 30 minutes, and 1 hour. All reactions were carried out at 37° C. Lane (i) 50 bp DNA ladder, (ii) 3WJ construct in standard melt buffer (1 M sodium chloride, 10 mM sodium cacodylate, 0.5 EDTA, pH 7) for 1 hour, (iii) 3WJ construct in 1000-fold diluted serum for 10 minutes, (iv) 3WJ construct in 1000-fold diluted serum for 30 minutes, (v) 3WJ construct in 1000-fold diluted serum for 1 hour. Both M2 and SF5 3WJ constructs were confirmed as more stable in human blood serum over time than the stem phi29 3WJ construct.

Melting Temperatures

Melting temperatures ($T_m$s) for various 3WJ constructs at approximately 40 μM were determined by UV optical melting as outlined above (Table 3). Error in $T_m$ is estimated to be ±1° C. The SF5, M2, phi29$_{\Delta U29/\Delta U72-73}$, SF5$_{\Delta G69}$, and SF5$_{\Delta G31/\Delta G-69}$ 3 WJ constructs have a significantly higher melting temperature than the stem phi29 3WJ construct at 40 μM, indicating higher stability.

TABLE 3

$T_m$s of Various 3WJ constructs

| Construct | Tm (C.) |
| --- | --- |
| phi29 | 55.81 |
| GA1 | 51.84 |
| SF5 | 58.61 |
| M2 | 59.07* |
| phi29$_{\Delta U29}$ | 55.87 |
| phi29$_{\Delta U72}$ | 56.25 |
| phi29$_{\Delta U72-73}$ | 56.44 |
| phi29$_{\Delta U72-73-74}$ | 56.47 |
| phi29$_{\Delta U29/\Delta U72}$ | 56.75 |
| phi29$_{\Delta U29/\Delta U72-73}$ | 58.83 |
| phi29$_{\Delta U29/\Delta U72-73-74}$ | 56.53 |
| SF5$_{\Delta G31}$ | 56.66* |
| SF5$_{\Delta G69}$ | 58.13 |
| SF5$_{\Delta G31/\Delta G69}$ | 59.03 |

*Melting temperatures for M2 and SF5ΔG31 are reported at concentrations of 25 μM and 33 μM, respectively.

EXAMPLES

The inventive concepts of the present disclosure, having now been generally described, will be more readily understood by reference to the following additional examples and embodiments, which are included merely for purposes of illustration of certain aspects and embodiments thereof, and are not intended to be limiting. The following detailed examples are to be construed, as noted above, only as illustrative, and not as limitations of the disclosure in any way whatsoever. Those skilled in the art will promptly recognize appropriate variations from the various constructs, nanoparticles, compositions, components, procedures and methods.

Included in the non-limiting examples below are three-sequence sets of pRNA oligonucleotides (3WJa, 3WJb, and 3WJc sequence strands, 5'→3') which may be used to assemble various 3WJ constructs which may be formed and used in accordance with the teachings of the present disclosure. Any of the three-sequence sets described below or elsewhere herein may be assembled into 3WJ scaffolds to which biologically-active moieties are covalently linked (via connection to one of more of the branches of the 3WJ) to form the conjugates used in accordance with the present disclosure.

In at least one embodiment, the present disclosure is directed to an RNA junction scaffold, comprising: a three-way junction (3WJ) construct, the 3WJ construct comprising a 3WJa sequence comprising a first RNA oligonucleotide, a 3WJb sequence comprising a second RNA oligonucleotide, and a 3WJc sequence comprising a third RNA oligonucleotide, wherein a first branch of the 3WJ construct is formed from a 5' portion of the 3WJa sequence and a 3' portion of the 3WJc sequence, a second branch of the 3WJ construct is formed from a 3' portion of the 3WJa sequence and a 5' portion of the 3WJb sequence, and a third branch of the 3WJ construct is formed from a 3' portion of the 3WJb sequence and a 5' portion of the 3WJc sequence, wherein each of said branches comprises a helical region having a plurality of RNA nucleotide pairs that form canonical Watson-Crick bonds.

In at least one embodiment of the RNA junction scaffold, the 3WJb sequence comprises a single unpaired nucleotide (e.g., U) in a position between the helical region of the second branch and the helical region of the third branch, or in the 3WJc sequence in a position between the helical region of the first branch and the helical region of the third branch.

In at least one embodiment of the RNA junction scaffold, the 3WJa sequence comprises only two adjacent unpaired nucleotides (e.g., CA) in the second branch, the 3WJb sequence comprises a single unpaired nucleotide (e.g., C) in a position between the helical region of the second branch and the helical region of the third branch, and the 3WJc sequence comprises only two adjacent unpaired nucleotides (e.g., CU) in a position between the helical region of the first branch and the helical region of the third branch.

In at least one embodiment of the RNA junction scaffold, the 3WJa sequence comprises a single unpaired nucleotide in the second branch (e.g., G), and the 3WJb sequence comprises only two unpaired nucleotides (e.g., GG) in a position between the helical region of the second branch and the helical region of the third branch.

In at least one embodiment of the RNA junction scaffold, the 3WJa sequence is absent an unpaired nucleotide in the second branch, and the 3WJb sequence comprises only two unpaired nucleotides (e.g., GG) in a position between the helical region of the second branch and the helical region of the third branch.

In at least one embodiment of the RNA junction scaffold, the 3WJa sequence is absent an unpaired nucleotide in the second branch, and the 3WJb sequence comprises only a single unpaired nucleotide (e.g., G) in a position between the helical region of the second branch and the helical region of the third branch.

In at least one embodiment of the RNA junction scaffold, the 3WJa sequence comprises a single unpaired nucleotide (e.g., G), and the 3WJb sequence comprises a single unpaired nucleotide (e.g., G) in a position between the helical region of the second branch and the helical region of the third branch.

In at least one embodiment of the RNA junction scaffold, the 3WJa sequence comprises a single unpaired nucleotide (e.g., G) in a position between the helical region of the first branch and the helical region of the second branch, and a single unpaired nucleotide (e.g., G) downstream of the first helical region, in a portion of the second branch (e.g., G), and the 3WJc sequence comprises a single unpaired nucleotide (e.g., A) in a position between the helical region of the first branch and the helical region of the third branch.

A stem phi29 pRNA 3WJ construct (FIG. 2) derived from a wild type phi29 pRNA comprises three unpaired nucleotides (UUU) in the 3WJb sequence in positions corresponding to positions 72, 73, and 74 of the entire wild type phi29 pRNA in a location between the helical region of the second branch and the helical region of the third branch, and comprises an unpaired nucleotide U in the 3WJa sequence in a position corresponding to position 29 in the wild type phi29 pRNA in a location between the helical region of the first branch and the helical region of the second branch (wherein position numbers correspond to the sequences of the entire wild type phi29 pRNA). At least one embodiment of the present disclosure is directed to a phi29 pRNA 3WJ deletion mutant construct (phi29$_{\Delta U29/\Delta U72-73}$ in FIG. 12) that lacks two of the unpaired nucleotides U (U72 and U73) in the 3WJb sequence in a position between the second helical region and the third helical region, and lacks the single unpaired nucleotide U (U29) in the 3WJa sequence between the first helical region and the second helical region.

A stem M2 3WJ construct (FIG. 14) derived from a wild type M2 pRNA comprises two adjacent unpaired nucleotides (AU) situated at positions 36 and 37 in the M2 3WJa sequence of the second branch and an unpaired nucleotide (A) situated at position 79 in the M2 3WJb sequence of the third branch of the construct (position numbers correspond to the sequences of the entire wild type M2 pRNA). At least one embodiment of the present disclosure is directed to an M2 pRNA 3WJ deletion mutant construct (M2$_{\Delta AUA}$) in FIG. 3) that lacks the two unpaired nucleotides AU which correspond to positions 36 and 37 in the WT 3WJa sequence of the second branch, and lacks the unpaired nucleotide A which corresponds to position 79 in the WT 3WJb sequence of the third branch of the construct.

A stem SF5 3WJ construct (FIG. 3) comprises an unpaired nucleotide (G) at position 31 of a 3WJa sequence of the second branch and two adjacent unpaired nucleotides (GG) at positions 69 and 70 of the 3WJb sequence in a location between the helical region of the second branch and the helical region of the third branch (position numbers correspond to the sequence of the entire wild type SF5 pRNA). Certain embodiments of the present disclosure are directed to SF5 pRNA 3WJ deletion mutant constructs that lacks one, two, or three of the unpaired nucleotides of the 3WJa and 3WJb sequences of the SF5 3WJ, such as G$_{31}$ (SF5$_{\Delta G31}$) of the 3WJa sequence (e.g., FIG. 32), G$_{69}$ (SF5$_{\Delta G69}$) of the 3WJB sequence, (e.g., FIG. 37), both G$_{31}$ and G$_{69}$ (SF5$_{\Delta G31/\Delta G69}$) of the 3WJa and 3WJb sequences (e.g., FIG. 42), or G$_{31}$, G$_{69}$, and G$_{70}$ (SF5$_{\Delta G31/\Delta G69-70}$) of the 3WJa and 3WJb sequences.

A stem GA1 3WJ construct (FIG. 2) derived from a wild type GA1 pRNA comprises a single unpaired nucleotide (G) situated at position 27 of the 3WJa sequence in a location between the helical region of the first branch and the helical region of the second, a single unpaired nucleotide (G) situated at position 32 of the 3WJa sequence in a location in the second branch of the construct, and a single unpaired nucleotide (A) situated at position 89 of the 3WJc sequence in a location between the helical region of the first branch and the helical region of the third branch (position numbers correspond to the sequences of the entire wild type GA1 pRNA). At least one embodiment of the present disclosure is directed to a GA1 pRNA 3WJ deletion mutant construct lacking an unpaired nucleotide at one of positions 27, 32, or 89, or lacking two unpaired nucleotides at positions 27 and 32, or 27 and 89, or 32 and 89.

The following are non-limiting examples of phi29 pRNA three-sequence sets (3WJa, 3WJb, and 3WJc sequence strands, 5'→3') which may be used to base pair various 3WJ constructs of the present disclosure (Examples 1-13 are represented in FIGS. 12, 13, and 15-26, and generically in FIGS. 48-49):

```
1. (FIG. 12)
                                        (SEQ ID NO: 13)
        3WJa:      CUUGUCAUGGUAUGUUGCC (SEQ ID NO: 15)
        3WJb:      GGCACAUACUGUUGAUAGG (SEQ ID NO: 3)
        3WJc:      CCUGUCAAUCAUGGCAAG 2. (FIG. 13)
                                        (SEQ ID NO: 13)
        3WJa:      CUUGUCAUGGUAUGUUGCC (SEQ ID NO: 16)
        3WJb:      GGCACAUACGUUGAUAGG (SEQ ID NO: 3)
        3WJc:      CCUGUCAAUCAUGGCAAG 2. (FIG. 15)
                                        (SEQ ID NO: 17)
        3WJa:      UUGUCAUGGUAUGUUGCC (SEQ ID NO: 15)
        3WJb:      GGCACAUACUGUUGAUAGG (SEQ ID NO: 18)
        3WJc:      CCUGUCAAUCAUGGCAA 3. (FIG. 16)
                                        (SEQ ID NO: 19)
        3WJa:      UUGUCAUGGUAUGUUGC (SEQ ID NO: 20)
        3WJb:      GCACAUACUGUUGAUAGG (SEQ ID NO: 18)
        3WJc:      CCUGUCAAUCAUGGCAA 4. (FIG. 17)
                                        (SEQ ID NO: 19)
        3WJa:      UUGUCAUGGUAUGUUGC (SEQ ID NO: 21)
        3WJb:      GCACAUACUGUUGAUAG (SEQ ID NO: 22)
        3WJc:      CUGUCAAUCAUGGCAA 5. (FIG. 18)
                                        (SEQ ID NO: 23)
        3WJa:      UGUCAUGGUAUGUUGC (SEQ ID NO: 21)
        3WJb:      GCACAUACUGUUGAUAG (SEQ ID NO: 24)
        3WJc:      CUGUCAAUCAUGGCA 6. (FIG. 19)
                                        (SEQ ID NO: 25)
        3WJa:      UGUCAUGGUAUGUUG (SEQ ID NO: 26)
        3WJb:      CACAUACUGUUGAUAG (SEQ ID NO: 24)
        3WJc:      CUGUCAAUCAUGGCA
```

-continued 7. (FIG. 20)

3WJa: UGUCAUGGUAUGUUG (SEQ ID NO: 25)

3WJb: CACAUACUGUUGAUA (SEQ ID NO: 27)

3WJc: UGUCAAUCAUGGCA (SEQ ID NO: 28)

8. (FIG. 21)

3WJa: GUCAUGGUAUGUUG (SEQ ID NO: 29)

3WJb: CACAUACUGUUGAUA (SEQ ID NO: 27)

3WJc: UGUCAAUCAUGGC (SEQ ID NO: 30)

9. (FIG. 22)

3WJa: GUCAUGGUAUGUU (SEQ ID NO: 31)

3WJb: ACAUACUGUUGAUA (SEQ ID NO: 32)

3WJc: UGUCAAUCAUGGC (SEQ ID NO: 30)

10. (FIG. 23)

3WJa: GUCAUGGUAUGUU (SEQ ID NO: 31)

3WJb: ACAUACUGUUGAU (SEQ ID NO: 33)

3WJc: GUCAAUCAUGGC (SEQ ID NO: 34)

11. (FIG. 24)

3WJa: UCAUGGUAUGUU (SEQ ID NO: 35)

3WJb: ACAUACUGUUGAU (SEQ ID NO: 33)

3WJc: GUCAAUCAUGG (SEQ ID NO: 36)

12. (FIG. 25)

3WJa: UCAUGGUAUG (SEQ ID NO: 37)

3WJb: CAUACUGUUGAU (SEQ ID NO: 38)

3WJc: GUCAAUCAUGG (SEQ ID NO: 36)

13. (FIG. 26)

3WJa: UCAUGGUAUG (SEQ ID NO: 37)

3WJb: CAUACUGUUGA (SEQ ID NO: 39)

3WJc: UCAAUCAUGG (SEQ ID NO: 40)

The following examples 14-32 are non-limiting examples of M2 pRNA three-sequence sets (3WJa, 3WJb, and 3WJc sequence strands, 5'→3') which may be used to base pair various 3WJ constructs of the present disclosure (Examples 14, 29-31, and 27 are represented in FIGS. 3, and 27-31, respectively, and generically in FIG. 50):

14: (FIG. 3)

3WJa: GCAAUAGUAUGGCACAUGUGC (SEQ ID NO: 10)

3WJb: GCACAUGUCACGGGGUAGG (SEQ ID NO: 11)

3WJc: CCUACCCUCUUACUAUUGC (SEQ ID NO: 12)

15:

3WJa: CAAUAGUAUGGCACAUGUGC (SEQ ID NO: 41)

3WJb: GCACAUGUCACGGGGUAGG (SEQ ID NO: 11)

3WJc: CCUACCCUCUUACUAUUG (SEQ ID NO: 42)

16:

3WJa: CAAUAGUAUGGCACAUGUG (SEQ ID NO: 43)

3WJb: CACAUGUCACGGGGUAGG (SEQ ID NO: 44)

3WJc: CCUACCCUCUUACUAUUG (SEQ ID NO: 42)

17:

3WJa: CAAUAGUAUGGCACAUGUG (SEQ ID NO: 43)

3WJb: CACAUGUCACGGGGUAGG (SEQ ID NO: 45)

3WJc: CUACCCUCUUACUAUUG (SEQ ID NO: 46)

18.

3WJa: AAUAGUAUGGCACAUGUG (SEQ ID NO: 47)

3WJb: CACAUGUCACGGGGUAGG (SEQ ID NO: 45)

3WJc: CUACCCUCUUACUAUU (SEQ ID NO: 48)

19.

3WJa: AAUAGUAUGGCACAUGU (SEQ ID NO: 49)

3WJb: ACAUGUCACGGGGUAGG (SEQ ID NO: 50)

3WJc: CUACCCUCUUACUAUU (SEQ ID NO: 48)

20.

3WJa: AAUAGUAUGGCACAUGU (SEQ ID NO: 49)

3WJb: ACAUGUCACGGGGUAG (SEQ ID NO: 51)

3WJc: UACCCUCUUACUAUU (SEQ ID NO: 52)

21.

3WJa: AUAGUAUGGCACAUGU (SEQ ID NO: 53)

3WJb: ACAUGUCACGGGGUAG (SEQ ID NO: 51)

3WJc: UACCCUCUUACUAU (SEQ ID NO: 54)

-continued 22.
3WJa: AUAGUAUGGCACAUG (SEQ ID NO: 55)
3WJb: CAUGUCACGGGUAG (SEQ ID NO: 56)
3WJc: UACCCUCUUACUAU (SEQ ID NO: 54)

23.
3WJa: AUAGUAUGGCACAUG (SEQ ID NO: 55)
3WJb: CAUGUCACGGGGUA (SEQ ID NO: 57)
3WJc: ACCCUCUUACUAU (SEQ ID NO: 58)

24.
3WJa: UAGUAUGGCACAUG (SEQ ID NO: 59)
3WJb: CAUGUCACGGGGUA (SEQ ID NO: 57)
3WJc: ACCCUCUUACUA (SEQ ID NO: 60)

25.
3WJa: UAGUAUGGCACAU (SEQ ID NO: 61)
3WJb: AUGUCACGGGUA (SEQ ID NO: 63)
3WJc: ACCCUCUUACUA (SEQ ID NO: 64)

26.
3WJa: UAGUAUGGCACAU (SEQ ID NO: 61)
3WJb: AUGUCACGGGG (SEQ ID NO: 63)
3WJc: CCCUCUUACUA (SEQ ID NO: 64)

27. (FIG. 30)
3WJa: UAGUAUGGCACA (SEQ ID NO: 65)
3WJb: UGUCACGGGG (SEQ ID NO: 66)
3WJc: CCCUCUUACUA (SEQ ID NO: 64)

28.
3WJa: UAGUAUGGCACA (SEQ ID NO: 65)
3WJb: UGUCACGGG (SEQ ID NO: 67)
3WJc: CCUCUUACUA (SEQ ID NO: 68)

29: (FIG. 27)
3WJa: CAAUAGUAUGGCACAUGUG (SEQ ID NO: 43)
3WJb: CACAUGUCACGGGGUAG (SEQ ID NO: 69)
3WJc: CUACCCUCUUACUAUUG (SEQ ID NO: 46)

30. (FIG. 28)
3WJa: AAUAGUAUGGCACAUGUG (SEQ ID NO: 47)
3WJb: CACAUGUCACGGGGUA (SEQ ID NO: 70)
3WJc: UACCCUCUUACUAUU (SEQ ID NO: 52)

31. (FIG. 29)
3WJa: AUAGUAUGGCACAUG (SEQ ID NO: 55)
3WJb: CAUGUCACGGGG (SEQ ID NO: 71)
3WJc: CCCUCUUACUAU (SEQ ID NO: 72)

32. (FIG. 31)
3WJa: AGUAUGGCAC (SEQ ID NO: 73)
3WJb: GUCACGGG (SEQ ID NO: 74)
3WJc: CCUCUUAC (SEQ ID NO: 75)

The following examples 33-47 are non-limiting examples of SF5 pRNA three-sequence sets (3WJa, 3WJb, and 3WJc sequence strands, 5'→3') which may be used to base pair various 3WJ constructs of the present disclosure (Examples 33-47 are represented in FIGS. 32-46, respectively, and generically in FIGS. 51-53):

33. (FIG. 32)
3WJa: GCUAAUGUAUGUUGUCCG (SEQ ID NO: 76)
3WJb: CGGACAGCAGGGGAGCGUGC (SEQ ID NO: 8)
3WJc: GCACACUCUUGCAUUAGC (SEQ ID NO: 9)

34. (FIG. 33)
3WJa: CUAAUGUAUGUUGUCC (SEQ ID NO: 77)
3WJb: GGACAGCAGGGGAGCGUG (SEQ ID NO: 78)
3WJc: CACACUCUUGCAUUAG (SEQ ID NO: 79)

35. (FIG. 34)
3WJa: UAAUGUAUGUUGUC (SEQ ID NO: 80)
3WJb: GACAGCAGGGGAGCGU (SEQ ID NO: 81)
3WJc: ACACUCUUGCAUUA (SEQ ID NO: 82)

36. (FIG. 35)
3WJa: AAUGUAUGUUGU (SEQ ID NO: 83)
3WJb: ACAGCAGGGGAGCG (SEQ ID NO: 84)
3WJc: CACUCUUGCAUU (SEQ ID NO: 85)

-continued 37. (FIG. 36)

```
                                        (SEQ ID NO: 86)
3WJa:      AUGUAUGUUG (SEQ ID NO: 87)
3WJb:      CAGCAGGGAGC (SEQ ID NO: 88)
3WJc:      ACUCUUGCAU
```

38. (FIG. 37)

```
                                        (SEQ ID NO: 7)
3WJa:      GCUAAUGUAUGUGUGUCCG (SEQ ID NO: 89)
3WJb:      CGGACAGCAGGGAGCGUGC (SEQ ID NO: 9)
3WJc:      GCACACUCUUGCAUUAGC
```

39. (FIG. 38)

```
                                        (SEQ ID NO: 90)
3WJa:      CUAAUGUAUGUGUGUCC (SEQ ID NO: 91)
3WJb:      GGACAGCAGGGAGCGUG (SEQ ID NO: 79)
3WJc:      CACACUCUUGCAUUAG
```

40. (FIG. 39)

```
                                        (SEQ ID NO: 92)
3WJa:      UAAUGUAUGUGUGUC (SEQ ID NO: 93)
3WJb:      GACAGCAGGGAGCGU (SEQ ID NO: 82)
3WJc:      ACACUCUUGCAUUA
```

41. (FIG. 40)

```
                                        (SEQ ID NO: 94)
3WJa:      AAUGUAUGUGUGU (SEQ ID NO: 95)
3WJb:      ACAGCAGGGAGCG (SEQ ID NO: 96)
3WJc:      CACUCUUGCAUU
```

42. (FIG. 41)

```
                                        (SEQ ID NO: 97)
3WJa:      AUGUAUGUGUG (SEQ ID NO: 98)
3WJb:      CAGCAGGGAGC (SEQ ID NO: 88)
3WJc:      ACUCUUGCAU
```

43. (FIG. 42)

```
                                        (SEQ ID NO: 76)
3WJa:      GCUAAUGUAUGUUGUCCG (SEQ ID NO: 89)
3WJb:      CGGACAGCAGGGAGCGUGC (SEQ ID NO: 9)
3WJc:      GCACACUCUUGCAUUAGC
```

44. (FIG. 43)

```
                                        (SEQ ID NO: 77)
3WJa:      CUAAUGUAUGUUGUCC (SEQ ID NO: 91)
3WJb:      GGACAGCAGGGAGCGUG (SEQ ID NO: 79)
3WJc:      CACACUCUUGCAUUAG
```

45. (FIG. 44)

```
                                        (SEQ ID NO: 80)
3WJa:      UAAUGUAUGUUGUC (SEQ ID NO: 93)
3WJb:      GACAGCAGGGAGCGU (SEQ ID NO: 82)
3WJc:      ACACUCUUGCAUUA
```

46. (FIG. 45)

```
                                        (SEQ ID NO: 83)
3WJa:      AAUGUAUGUUGU (SEQ ID NO: 95)
3WJb:      ACAGCAGGGAGCG (SEQ ID NO: 85)
3WJc:      CACUCUUGCAUU
```

47. (FIG. 46)

```
                                        (SEQ ID NO: 86)
3WJa:      AUGUAUGUUG (SEQ ID NO: 98)
3WJb:      CAGCAGGGAGC (SEQ ID NO: 88)
3WJc:      ACUCUUGCAU
```

The following example 48 is a non-limiting example of GA1 pRNA three-sequence sets (3WJa, 3WJb, and 3WJc sequence strands, 5'→3') which may be used to base pair various 3WJ constructs of the present disclosure (Example 48 is represented in FIG. 47 and generically in FIG. 54):

48. (FIG. 47)

```
                                        (SEQ ID NO: 99)
3WJa:      UAUAGGCUGUGCA (SEQ ID NO: 100)
3WJb:      UGACAGGUUGU (SEQ ID NO: 101)
3WJc:      GCAAUACUAUA
```

The following Examples 49-56 are non-limiting generic representations pRNA three-sequence sets (3WJa, 3WJb, and 3WJc sequence strands, 5'→3') which may be used to base pair various 3WJ constructs of the present disclosure, including Examples 49-50 (FIGS. 48-49) for phi29 3WJ, Example 51 (FIG. 50) for M2 3WJ, Example 52-55 (FIGS. 51-53) for SF5 3WJs, and Example 56 (FIG. 54) for GA1 3WJ. W and C represent nucleotides which form pairs when assembled in the 3WJ from the 3WJa, 3WJb, and 3WJc strands and N represents an unpaired nucleotide in the assembled 3WJ.

49. (FIG. 48)

```
                                        (SEQ ID NO: 102)
3WJa:      WWWWWWWWW (SEQ ID NO: 103)
3WJb:      CCCCCNCCCCC (SEQ ID NO: 104)
3WJc:      WWWWWCCCCC
```

50. (FIG. 49)

```
                                        (SEQ ID NO: 102)
3WJa:      WWWWWWWWW (SEQ ID NO: 105)
3WJb:      CCCCCCCCCC
```

-continued

```
                                       (SEQ ID NO: 106)
3WJc:           WWWWWNCCCCC 51. (FIG. 50)
                                       (SEQ ID NO: 107)
3WJa:           WWWWWWWWNNWW (SEQ ID NO: 103)
3WJb:           CCCCCNCCCCC (SEQ ID NO: 108)
3WJc:           WWWWWNNCCCCC 52. (FIG. 51)
                                       (SEQ ID NO: 109)
3WJa:           WWWWWWWWNWW (SEQ ID NO: 110)
3WJb:           CCCCCNNCCCCC (SEQ ID NO: 104)
3WJc:           WWWWWCCCCC 53. (FIG. 52)
                                       (SEQ ID NO: 102)
3WJa:           WWWWWWWWWW (SEQ ID NO: 110)
3WJb:           CCCCCNNCCCCC (SEQ ID NO: 104)
3WJc:           WWWWWCCCCC 54. (FIG. 53)
                                       (SEQ ID NO: 109)
3WJa:           WWWWWWWWNWW (SEQ ID NO: 103)
3WJb:           CCCCCNCCCCC (SEQ ID NO: 104)
3WJc:           WWWWWCCCCC 55.
                                       (SEQ ID NO: 102)
3WJa:           WWWWWWWWWW (SEQ ID NO: 103)
3WJb:           CCCCCNCCCCC (SEQ ID NO: 104)
3WJc:           WWWWWCCCCC 56. (FIG. 54)
                                       (SEQ ID NO: 109)
3WJa:           WWWWWWWWNWW (SEQ ID NO: 105)
3WJb:           CCCCCCCCCC (SEQ ID NO: 106)
3WJc:           WWWWWNCCCCC
```

FIGS. 48-49 (Examples 49-50) depict embodiments of a generic phi29 pRNA 3WJ mutant constructs of the present disclosure. As explained above, each 3WJ construct comprises three branches, each comprising a helical region, with each helical region comprising a plurality nucleotide base pairs (W-C) forming canonical Watson-Crick bonds (e.g., G-C, C-G, U-A, A-U), and which also may contain a single unpaired nucleotide N (i.e., C, G, A, or U) in a position in the 3WJb sequence between the helical region of the second branch and the helical region of the third branch as shown in FIG. 48, or in a position in the 3WJc sequence between the helical region of the first branch and the helical region of the third branch as shown in FIG. 49. Non-Watson-Crick nucleotide base pairs which may occur in one or more of the branches of the 3WJs of FIGS. 48 and 49 include, for example, G-U, U-G, U-C, C-U, G-A, A-G, A-C, and C-A.

FIG. 50 (Example 51) depicts an embodiment of a generic M2 pRNA 3WJ mutant construct of the present disclosure. The M2 3WJ construct comprises three branches, each comprising a helical region, with each helical region comprising a plurality of nucleotide base pairs (W-C) forming canonical Watson-Crick bonds (e.g., G-C, C-G, U-A, A-U), and which also contains two adjacent unpaired nucleotides N (i.e., C, G, A, or U) in 3WJa in the second branch, a single unpaired nucleotide N (i.e., C, G, A, or U) in a position in the 3WJb sequence between the helical region of the second branch and the helical region of the third branch, and a pair of adjacent unpaired nucleotides N (e.g., selected from C, G, A, and U) in a position in the 3WJc sequence between the helical region of the third branch and the helical region of the first branch as shown in FIG. 50. Non-Watson-Crick nucleotide base pairs which may occur in one or more of the branches of the 3WJs of FIG. 50 include, for example, G-U, U-G, U-C, C-U, G-A, A-G, A-C, and C-A.

FIGS. 51-53 (Examples 52-55) depict embodiments of a generic SF5 pRNA 3WJ mutant construct of the present disclosure. The SF5 3WJ construct comprises three branches, each comprising a helical region, with each helical region comprising a plurality of nucleotide base pairs (W-C) forming canonical Watson-Crick bonds (e.g., G-C, C-G, U-A, A-U). The embodiment of FIG. 51 contains a single unpaired nucleotide N (i.e., C, G, A, or U) in 3WJa in the second branch, and two adjacent unpaired nucleotides N (i.e., C, G, A, or U) in 3WJb in a position between the helical region of the second branch and the helical region of the third branch. The embodiment of FIG. 52 contains two adjacent unpaired nucleotides N (i.e., C, G, A, or U) in 3WJb in a position between the helical region of the second branch and the helical region of the third branch. The embodiment of FIG. 53 contains a single unpaired nucleotide N (i.e., C, G, A, or U) in 3WJa in the second branch, and a single unpaired nucleotide N (i.e., C, G, A, or U) in 3WJb in a position between the helical region of the second branch and the helical region of the third branch. The embodiment of Example 54 is similar to FIGS. 51-53 except the 3WJ construct contains only a single unpaired nucleotide N (i.e., C, G, A, or U) in 3WJb in a position between the helical region of the second branch and the helical region of the third branch, and lacks unpaired nucleotides which correspond to G31 in the second branch and G69 in a position between the helical region of the second branch and the helical region of the third branch. Non-Watson-Crick nucleotide base pairs which may occur in one or more of the branches of the 3WJs of FIGS. 51-53 and Example 54 include, for example, G-U, U-G, U-C, C-U, G-A, A-G, A-C, and C-A.

FIG. 54 (Example 56) depicts an embodiment of a generic GA1 pRNA 3WJ mutant construct of the present disclosure. The GA1 3WJ construct comprises three branches, each comprising a helical region, with each helical region comprising a plurality of nucleotide base pairs (W-C) forming canonical Watson-Crick bonds (e.g., G-C, C-G, U-A, A-U). The embodiment of FIG. 54 contains a single unpaired nucleotide N (i.e., C, G, A, or U) in 3WJa in a position between the helical region of the first branch and the helical region of the second branch, a single unpaired nucleotide N (i.e., C, G, A, or U) in 3WJa in the second branch, and single unpaired nucleotide N (i.e., C, G, A, or U) in 3WJc in a position between the helical region of the first branch and the helical region of the third branch.

Furthermore, individual 3WJa, 3WJb, and 3WJc strands disclosed herein may be combined in three-sequence sets different from the combinations shown explicitly in the examples. For example, for alternate M2 3WJ constructs, SEQ ID NOS: 61, 63, and 64 could be combined, or SEQ ID NOS: 65, 63, and 60 could be combined. Similar alternate combinations could be made for phi29 and SF5 3WJ constructs.

As noted above, the pRNA 3WJ constructs described above can be used as a scaffold to which is linked, via the one or more branches, at least one biologically active moiety to form a conjugate, complex, or nanoparticle. At least one embodiment of the present disclosure is directed to a multivalent oligomeric complex comprising a plurality of monomers, each monomer comprising an RNA 3WJ scaffold to which at least one biologically-active moiety is linked. As described elsewhere herein, the biologically active moiety may be a therapeutic drug, antibody, marker, dye, siRNA, ribozyme, riboswitch, and/or aptamer. The therapeutic drug, antibody, marker, dye, siRNA, ribozyme, riboswitch, and/or aptamer may be linked, directly, or via a linker molecule such as an oligonucleotide, to one of the three oligonucleotide sequences 3WJa, 3WJb, or 3WJc before the three oligonucleotide sequences 3WJa, 3WJb, and 3WJc are combined in a mixture and self-assemble into the 3WJ. One, two, or three of the oligonucleotide sequences 3WJa, 3WJb, and 3WJc may be linked to a therapeutic drug, antibody, marker, dye, siRNA, ribozyme, riboswitch, and/or aptamer to form the conjugate, complex, or nanoparticle. Non-RNA moieties can be linked to the pRNA 3WJ domains in any suitable manner. For example, folate can be conjugated into adenosine 5'-monophosphate (AMP) by 1,6-hexanediamine linkages. After reverse HPLC to reach 93% purity, the folate-AMP can be incorporated into the 5'-end of the phi29 pRNA. For example, a 16:1 ratio of folate-AMP to ATP in transcription resulted in more than 60% of the pRNA containing folate (Gene Ther. 2006 May; 13(10):814-20.). Numerous other methods for conjugation of chemicals to RNA are known to persons having ordinary skill in the art, such as are shown in Chem Soc Rev. 2010 June; 39(6):2054-70. Other linking methods and biologically-active moieties are shown in U.S. Pat. No. 9,297,013 B2.

In accordance with the foregoing, the present disclosure is directed to, in at least certain embodiments:

Clause 1. An RNA junction scaffold comprising a three-way junction (3WJ) domain, the 3WJ domain comprising a 3WJa sequence comprising a first RNA polynucleotide, a 3WJb sequence comprising a second RNA polynucleotide, and a 3WJc sequence comprising a third RNA polynucleotide, wherein a first branch of the 3WJ domain is formed from a 5' portion of the 3WJa sequence and a 3' portion of the 3WJc sequence and comprises a first helical region, a second branch of the 3WJ domain is formed from a 3' portion of the 3WJa sequence and a 5' portion of the 3WJb sequence and comprises a second helical region, and a third branch of the 3WJ domain is formed from a 3' portion of the 3WJb sequence and a 5' portion of the 3WJc sequence and comprises a third helical region, wherein each of said helical regions comprises a plurality of RNA nucleotide pairs that form canonical Watson-Crick bonds, and wherein (i) the 3WJa sequence is absent an unpaired nucleotide positioned between the first helical region and the second helical region, and two unpaired nucleotides are positioned in the 3WJa sequence in the second branch, and (ii) two adjacent unpaired nucleotides are positioned in the 3WJc sequence between the first helical region and the third helical region, and one unpaired nucleotide is positioned in the 3WJb sequence between the second helical region and the third helical region.

Clause 2. The RNA junction scaffold of clause 1, wherein the 3WJa sequence comprises SEQ ID NO:73, the 3WJb sequence comprises SEQ ID NO:74, and the 3WJc sequence comprises SEQ ID NO:75.

Clause 3. The RNA junction scaffold of either clause 1 or 2, wherein the second branch is absent adjacent unpaired nucleotides in positions corresponding to unpaired adenine and uracil nucleotides in positions 36 and 37, respectively, of a wild type M2 pRNA, and wherein the third branch is absent an unpaired nucleotide in a position corresponding to an unpaired adenine nucleotide in position 79 of said wild type M2 pRNA.

Clause 4. The RNA junction scaffold of any one of clauses 1-3, absent one or more unpaired nucleotides in the 3WJa sequence downstream of the two unpaired nucleotides present in the 3WJa sequence.

Clause 5. The RNA junction scaffold of any one of clauses 1-4, absent an unpaired nucleotide in the 3WJb sequence downstream of the unpaired nucleotide present in the 3WJb sequence.

Clause 6. The RNA junction scaffold of any one of clauses 1-5, absent one or more unpaired nucleotides in the 3WJa sequence downstream of the two unpaired nucleotides present in the 3WJa sequence, and absent an unpaired nucleotide in the 3WJb sequence downstream of the unpaired nucleotide present in the 3WJb sequence.

Clause 7. An RNA junction scaffold, comprising: a three-way junction (3WJ) domain, the 3WJ domain comprising a 3WJa sequence comprising a first RNA polynucleotide, a 3WJb sequence comprising a second RNA polynucleotide, and a 3WJc sequence comprising a third RNA polynucleotide, wherein a first branch of the 3WJ domain is formed from a 5' portion of the 3WJa sequence and a 3' portion of the 3WJc sequence and comprises a first helical region, a second branch of the 3WJ domain is formed from a 3' portion of the 3WJa sequence and a 5' portion of the 3WJb sequence and comprises a second helical region, and a third branch of the 3WJ domain is formed from a 3' portion of the 3WJb sequence and a 5' portion of the 3WJc sequence and comprises a third helical region, wherein each of said helical regions comprises a plurality of RNA nucleotide pairs that form canonical Watson-Crick bonds, and wherein (i) the 3WJa sequence is absent an unpaired nucleotide positioned between the first helical region and the second helical region, and one unpaired nucleotide is positioned in the 3WJa sequence in the second branch, and (ii) two adjacent unpaired nucleotides are positioned in the 3WJb sequence between the second helical region and the third helical region.

Clause 8. An RNA junction scaffold, comprising: a three-way junction (3WJ) domain, the 3WJ domain comprising a 3WJa sequence comprising a first RNA polynucleotide, a 3WJb sequence comprising a second RNA polynucleotide, and a 3WJc sequence comprising a third RNA polynucleotide, wherein a first branch of the 3WJ domain is formed from a 5' portion of the 3WJa sequence and a 3' portion of the 3WJc sequence and comprises a first helical region, a second branch of the 3WJ domain is formed from a 3' portion of the 3WJa sequence and a 5' portion of the 3WJb sequence and comprises a second helical region, and a third branch of the 3WJ domain is formed from a 3' portion of the 3WJb sequence and a 5' portion of the 3WJc sequence and comprises a third helical region, wherein each of said helical regions comprises a plurality of RNA nucleotide pairs that form canonical Watson-Crick bonds, and wherein the 3WJa sequence is absent an unpaired nucleotide positioned between the first helical region and the second helical region, and is absent at least one of (1) an unpaired nucleotide in a position corresponding to an unpaired guanine nucleotide in position 31 of a wild type SF5 pRNA, and (2) an unpaired nucleotide in a position corresponding to an unpaired guanine nucleotide in position 69 of said wild type SF5 pRNA.

Clause 9. The RNA junction scaffold of clause 8, absent an unpaired nucleotide in a position corresponding to an unpaired guanine nucleotide in position 31 of a wild type SF5 pRNA.

Clause 10. The RNA junction scaffold of either clause 8 or 9, wherein the 3WJa sequence comprises SEQ ID NO:86, the 3WJb sequence comprises SEQ ID NO:87, and the 3WJc sequence comprises SEQ ID NO:88.

Clause 11. The RNA junction scaffold of any one of clauses 8-10, absent an unpaired nucleotide in a position corresponding to an unpaired guanine nucleotide in position 69 of said wild type SF5 pRNA.

Clause 12. The RNA junction scaffold of any one of clauses 8-11, wherein the 3WJa sequence comprises SEQ ID NO:97, the 3WJb sequence comprises SEQ ID NO:98, and the 3WJc sequence comprises SEQ ID NO:88.

Clause 13. The RNA junction scaffold of any one of clauses 8-12, absent (1) an unpaired nucleotide in a position corresponding to an unpaired nucleotide in position 31 of a wild type SF5 pRNA, and (2) an unpaired guanine nucleotide in a position corresponding to an unpaired guanine nucleotide in position 69 of said wild type SF5 pRNA.

Clause 14. The RNA junction scaffold of any one of clauses 8-13, wherein the 3WJa sequence comprises SEQ ID NO:86, the 3WJb sequence comprises SEQ ID NO:98, and the 3WJc sequence comprises SEQ ID NO:88.

Clause 15. An RNA junction scaffold, comprising: a three-way junction (3WJ) domain, the 3WJ domain comprising a 3WJa sequence comprising a first RNA polynucleotide, a 3WJb sequence comprising a second RNA polynucleotide, and a 3WJc sequence comprising a third RNA polynucleotide, wherein a first branch of the 3WJ domain is formed from a 5' portion of the 3WJa sequence and a 3' portion of the 3WJc sequence and comprises a first helical region, a second branch of the 3WJ domain is formed from a 3' portion of the 3WJa sequence and a 5' portion of the 3WJb sequence and comprises a second helical region, and a third branch of the 3WJ domain is formed from a 3' portion of the 3WJb sequence and a 5' portion of the 3WJc sequence and comprises a third helical region, wherein each of said helical regions comprises a plurality of RNA nucleotide pairs that form canonical Watson-Crick bonds, and wherein the 3WJa sequence is absent an unpaired nucleotide in a position between the first helical region and the second helical region corresponding to an unpaired uridine nucleotide in position 29 of a wild type phi29 pRNA positioned, and is absent two unpaired nucleotides in positions corresponding to two unpaired uridine nucleotides in positions 72 and 73 of said wild type phi29 pRNA.

Clause 16. The RNA junction scaffold of clause 15, wherein the 3WJa sequence comprises SEQ ID NO:37, the 3WJb sequence comprises SEQ ID NO:39, and the 3WJc sequence comprises SEQ ID NO:40.

Clause 17. An RNA junction scaffold, comprising: a three-way junction (3WJ) domain, the 3WJ domain comprising a 3WJa sequence comprising a first RNA polynucleotide, a 3WJb sequence comprising a second RNA polynucleotide, and a 3WJc sequence comprising a third RNA polynucleotide, wherein a first branch of the 3WJ domain is formed from a 5' portion of the 3WJa sequence and a 3' portion of the 3WJc sequence and comprises a first helical region, a second branch of the 3WJ domain is formed from a 3' portion of the 3WJa sequence and a 5' portion of the 3WJb sequence and comprises a second helical region, and a third branch of the 3WJ domain is formed from a 3' portion of the 3WJb sequence and a 5' portion of the 3WJc sequence and comprises a third helical region, wherein each of said helical regions comprises a plurality of RNA nucleotide pairs that form canonical Watson-Crick bonds, and wherein (i) the 3WJa sequence comprises a single unpaired nucleotide positioned between the first helical region and the second helical region, and an unpaired nucleotide positioned in the 3WJa sequence in the second branch downstream of the unpaired nucleotide positioned between the first helical region and the second helical region, and (ii) a single unpaired nucleotide positioned in the 3WJc sequence between the first helical region and the third helical region.

Clause 18. The RNA junction scaffold of clause 17, wherein the 3WJa sequence comprises SEQ ID NO:99, the 3WJb sequence comprises SEQ ID NO:100, and the 3WJc sequence comprises SEQ ID NO:101.

Clause 19. An RNA junction scaffold, comprising: a three-way junction (3WJ) domain, the 3WJ domain comprising a 3WJa sequence comprising a first RNA polynucleotide, a 3WJb sequence comprising a second RNA polynucleotide, and a 3WJc sequence comprising a third RNA polynucleotide, wherein a first branch of the 3WJ domain is formed from a 5' portion of the 3WJa sequence and a 3' portion of the 3WJc sequence and comprises a first helical region, a second branch of the 3WJ domain is formed from a 3' portion of the 3WJa sequence and a 5' portion of the 3WJb sequence and comprises a second helical region, and a third branch of the 3WJ domain is formed from a 3' portion of the 3WJb sequence and a 5' portion of the 3WJc sequence and comprises a third helical region, wherein each of said helical regions comprises a plurality of RNA nucleotide pairs that form canonical Watson-Crick bonds, and wherein (i) zero or one unpaired nucleotide is positioned in the 3WJa sequence between the first helical region and the second helical region, and/or one or two unpaired nucleotides are positioned in the 3WJa sequence in the second branch, and (ii) one unpaired or two adjacent unpaired nucleotides are positioned in the 3WJc sequence between the first helical region and the third helical region, and/or one unpaired or two adjacent unpaired nucleotides are positioned in the 3WJb sequence between the second helical region and the third helical region.

Clause 20. A conjugate comprising the RNA 3WJ scaffold of any one of clauses 1-19 linked to at least one moiety selected from the group consisting of therapeutic drugs, antibodies, markers, dyes, siRNAs, ribozymes, riboswitches, and aptamers.

Clause 21. A composition, comprising the conjugate of clause 20, and a pharmaceutically-acceptable vehicle, carrier, or diluent.

Clause 22: The RNA junction scaffold of any one of clauses 1-19, wherein each of the 3WJa, 3WJb, and 3WJc sequences comprises, independently, from 8 to 36 nucleotides, not including RNA linkers or an RNA portion of a biologically-active moiety conjugated to the RNA scaffold.

The pRNA 3WJ scaffolds, compounds, conjugates, compositions, nanoparticles, and methods of production and application thereof disclosed herein can be made and executed without undue experimentation in light of the present disclosure. While the present disclosure has been described in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure. Thus the examples described above, which include particular embodiments, will serve to illustrate the practice of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the presently disclosed methods and compositions. Changes may be made in the formulation of the various compositions described herein, the methods described herein or in the steps or the sequence of steps of the methods described herein without departing from the spirit and scope of the present disclosure.

SEQUENCE LISTING

```
<160> NUMBER OF SEQ ID NOS: 110

<210> SEQ ID NO 1
<211> LENGTH: 20
<212> TYPE: RNA
<213> ORGANISM: Bacillus page phi29

<400> SEQUENCE: 1
cuugucaugu guauguugcc                                               20

<210> SEQ ID NO 2
<211> LENGTH: 21
<212> TYPE: RNA
<213> ORGANISM: Bacillus phage phi29

<400> SEQUENCE: 2
ggcacauacu uuguugauag g                                             21

<210> SEQ ID NO 3
<211> LENGTH: 18
<212> TYPE: RNA
<213> ORGANISM: Bacillus phage phi29

<400> SEQUENCE: 3
ccugucaauc auggcaag                                                 18

<210> SEQ ID NO 4
<211> LENGTH: 23
<212> TYPE: RNA
<213> ORGANISM: Bacillus phage GA-1

<400> SEQUENCE: 4
cgauauauag gcugugcaag auu                                           23

<210> SEQ ID NO 5
<211> LENGTH: 20
<212> TYPE: RNA
<213> ORGANISM: Bacillus phage GA-1

<400> SEQUENCE: 5
aaucuugaca gguuguuggc                                               20

<210> SEQ ID NO 6
<211> LENGTH: 20
<212> TYPE: RNA
<213> ORGANISM: Bacillus phage GA-1

<400> SEQUENCE: 6
gcuagcaaua cuauauaucg                                               20

<210> SEQ ID NO 7
<211> LENGTH: 19
<212> TYPE: RNA
```

```
<213> ORGANISM: Bacillus phage SF5

<400> SEQUENCE: 7
gcuaauguau guguguccg                                                    19

<210> SEQ ID NO 8
<211> LENGTH: 20
<212> TYPE: RNA
<213> ORGANISM: Bacillus phage SF5

<400> SEQUENCE: 8
cggacagcag gggagcgugc                                                   20

<210> SEQ ID NO 9
<211> LENGTH: 18
<212> TYPE: RNA
<213> ORGANISM: Bacillus phage SF5

<400> SEQUENCE: 9
gcacacucuu gcauuagc                                                     18

<210> SEQ ID NO 10
<211> LENGTH: 21
<212> TYPE: RNA
<213> ORGANISM: Artificial Sequence
<220> FEATURE:
<223> OTHER INFORMATION: M2

<400> SEQUENCE: 10
gcaauaguau ggcacaugug c                                                 21

<210> SEQ ID NO 11
<211> LENGTH: 19
<212> TYPE: RNA
<213> ORGANISM: Artificial Sequence
<220> FEATURE:
<223> OTHER INFORMATION: M2

<400> SEQUENCE: 11
gcacauguca cggggguagg                                                   19

<210> SEQ ID NO 12
<211> LENGTH: 19
<212> TYPE: RNA
<213> ORGANISM: Artificial Sequence
<220> FEATURE:
<223> OTHER INFORMATION: M2

<400> SEQUENCE: 12 ccucccucu uacuauugc                                                     19

<210> SEQ ID NO 13
<211> LENGTH: 19
<212> TYPE: RNA
<213> ORGANISM: Artificial Sequence
<220> FEATURE:
<223> OTHER INFORMATION: Phi29

<400> SEQUENCE: 13
cuugucaugg uauguugcc                                                    19

<210> SEQ ID NO 14
<211> LENGTH: 20
<212> TYPE: RNA
<213> ORGANISM: Artificial Sequence
```

```
<220> FEATURE:
<223> OTHER INFORMATION: Phi29

<400> SEQUENCE: 14
ggcacauacu uguugauagg                                              20

<210> SEQ ID NO 15
<211> LENGTH: 19
<212> TYPE: RNA
<213> ORGANISM: Artificial Sequence
<220> FEATURE:
<223> OTHER INFORMATION: Phi29

<400> SEQUENCE: 15
ggcacauacu guugauagg                                               19

<210> SEQ ID NO 16
<211> LENGTH: 18
<212> TYPE: RNA
<213> ORGANISM: Artificial Sequence
<220> FEATURE:
<223> OTHER INFORMATION: Phi29

<400> SEQUENCE: 16
ggcacauacg uugauagg                                                18

<210> SEQ ID NO 17
<211> LENGTH: 18
<212> TYPE: RNA
<213> ORGANISM: Artificial Sequence
<220> FEATURE:
<223> OTHER INFORMATION: Phi29

<400> SEQUENCE: 17
uugucauggu auguugcc                                                18

<210> SEQ ID NO 18
<211> LENGTH: 17
<212> TYPE: RNA
<213> ORGANISM: Artificial Sequence
<220> FEATURE:
<223> OTHER INFORMATION: Phi29

<400> SEQUENCE: 18
ccugucaauc auggcaa                                                 17

<210> SEQ ID NO 19
<211> LENGTH: 17
<212> TYPE: RNA
<213> ORGANISM: Artificial Sequence
<220> FEATURE:
<223> OTHER INFORMATION: Phi29

<400> SEQUENCE: 19
uugucauggu auguugc                                                 17

<210> SEQ ID NO 20
<211> LENGTH: 18
<212> TYPE: RNA
<213> ORGANISM: Artificial Sequence
<220> FEATURE:
<223> OTHER INFORMATION: Phi29

<400> SEQUENCE: 20
gcacauacug uugauagg                                                18
```

```
<210> SEQ ID NO 21
<211> LENGTH: 17
<212> TYPE: RNA
<213> ORGANISM: Artificial Sequence
<220> FEATURE:
<223> OTHER INFORMATION: Phi29

<400> SEQUENCE: 21
gcacauacug uugauag                                                    17

<210> SEQ ID NO 22
<211> LENGTH: 16
<212> TYPE: RNA
<213> ORGANISM: Artificial Sequence
<220> FEATURE:
<223> OTHER INFORMATION: Phi29

<400> SEQUENCE: 22
cugucaauca uggcaa                                                     16

<210> SEQ ID NO 23
<211> LENGTH: 16
<212> TYPE: RNA
<213> ORGANISM: Artificial Sequence
<220> FEATURE:
<223> OTHER INFORMATION: Phi29

<400> SEQUENCE: 23
ugucauggua uguugc                                                     16

<210> SEQ ID NO 24
<211> LENGTH: 15
<212> TYPE: RNA
<213> ORGANISM: Artificial Sequence
<220> FEATURE:
<223> OTHER INFORMATION: Phi29

<400> SEQUENCE: 24
cugucaauca uggca                                                      15

<210> SEQ ID NO 25
<211> LENGTH: 15
<212> TYPE: RNA
<213> ORGANISM: Artificial Sequence
<220> FEATURE:
<223> OTHER INFORMATION: Phi29

<400> SEQUENCE: 25
ugucauggua uguug                                                      15

<210> SEQ ID NO 26
<211> LENGTH: 16
<212> TYPE: RNA
<213> ORGANISM: Artificial Sequence
<220> FEATURE:
<223> OTHER INFORMATION: Phi 29

<400> SEQUENCE: 26
cacauacugu ugauag                                                     16

<210> SEQ ID NO 27
<211> LENGTH: 15
<212> TYPE: RNA
<213> ORGANISM: Artificial Sequence
<220> FEATURE:
<223> OTHER INFORMATION: Phi29
```

-continued

```
<400> SEQUENCE: 27
cacauacugu ugaua                                                    15

<210> SEQ ID NO 28
<211> LENGTH: 14
<212> TYPE: RNA
<213> ORGANISM: Artificial Sequence
<220> FEATURE:
<223> OTHER INFORMATION: Phi29

<400> SEQUENCE: 28
ugucaaucau ggca                                                     14

<210> SEQ ID NO 29
<211> LENGTH: 14
<212> TYPE: RNA
<213> ORGANISM: Artificial Sequence
<220> FEATURE:
<223> OTHER INFORMATION: Phi29

<400> SEQUENCE: 29
gucaugguau guug                                                     14

<210> SEQ ID NO 30
<211> LENGTH: 13
<212> TYPE: RNA
<213> ORGANISM: Artificial Sequence
<220> FEATURE:
<223> OTHER INFORMATION: Phi29

<400> SEQUENCE: 30
ugucaaucau ggc                                                      13

<210> SEQ ID NO 31
<211> LENGTH: 13
<212> TYPE: RNA
<213> ORGANISM: Artificial Sequence
<220> FEATURE:
<223> OTHER INFORMATION: Phi29

<400> SEQUENCE: 31
gucaugguau guu                                                      13

<210> SEQ ID NO 32
<211> LENGTH: 14
<212> TYPE: RNA
<213> ORGANISM: Artificial Sequence
<220> FEATURE:
<223> OTHER INFORMATION: Phi29

<400> SEQUENCE: 32
acauacuguu gaua                                                     14

<210> SEQ ID NO 33
<211> LENGTH: 13
<212> TYPE: RNA
<213> ORGANISM: Artificial Sequence
<220> FEATURE:
<223> OTHER INFORMATION: Phi29

<400> SEQUENCE: 33
acauacuguu gau                                                      13

<210> SEQ ID NO 34
```

```
<211> LENGTH: 12
<212> TYPE: RNA
<213> ORGANISM: Artificial Sequence
<220> FEATURE:
<223> OTHER INFORMATION: Phi29

<400> SEQUENCE: 34
gucaaucaug gc                                                              12

<210> SEQ ID NO 35
<211> LENGTH: 12
<212> TYPE: RNA
<213> ORGANISM: Artificial Sequence
<220> FEATURE:
<223> OTHER INFORMATION: Phi29

<400> SEQUENCE: 35
ucaugguaug uu                                                              12

<210> SEQ ID NO 36
<211> LENGTH: 11
<212> TYPE: RNA
<213> ORGANISM: Artificial Sequence
<220> FEATURE:
<223> OTHER INFORMATION: Phi29

<400> SEQUENCE: 36
gucaaucaug g                                                               11

<210> SEQ ID NO 37
<211> LENGTH: 11
<212> TYPE: RNA
<213> ORGANISM: Artificial Sequence
<220> FEATURE:
<223> OTHER INFORMATION: Phi29

<400> SEQUENCE: 37
gucaaucaug g                                                               11

<210> SEQ ID NO 38
<211> LENGTH: 12
<212> TYPE: RNA
<213> ORGANISM: Artificial Sequence
<220> FEATURE:
<223> OTHER INFORMATION: Phi29

<400> SEQUENCE: 38
cauacuguug au                                                              12

<210> SEQ ID NO 39
<211> LENGTH: 11
<212> TYPE: RNA
<213> ORGANISM: Artificial Sequence
<220> FEATURE:
<223> OTHER INFORMATION: Phi29

<400> SEQUENCE: 39
cauacuguug a                                                               11

<210> SEQ ID NO 40
<211> LENGTH: 10
<212> TYPE: RNA
<213> ORGANISM: Artificial Sequence
<220> FEATURE:
<223> OTHER INFORMATION: Phi29

<400> SEQUENCE: 40
```

```
ucaaucaugg                                                          10

<210> SEQ ID NO 41
<211> LENGTH: 20
<212> TYPE: RNA
<213> ORGANISM: Artificial Sequence
<220> FEATURE:
<223> OTHER INFORMATION: M2

<400> SEQUENCE: 41
caauaguaug gcacaugugc                                               20

<210> SEQ ID NO 42
<211> LENGTH: 18
<212> TYPE: RNA
<213> ORGANISM: Artificial Sequence
<220> FEATURE:
<223> OTHER INFORMATION: M2

<400> SEQUENCE: 42
ccuacccucu uacuauug                                                 18

<210> SEQ ID NO 43
<211> LENGTH: 19
<212> TYPE: RNA
<213> ORGANISM: Artificial Sequence
<220> FEATURE:
<223> OTHER INFORMATION: M2

<400> SEQUENCE: 43
caauaguaug gcacaugug                                                19

<210> SEQ ID NO 44
<211> LENGTH: 18
<212> TYPE: RNA
<213> ORGANISM: Artificial Sequence
<220> FEATURE:
<223> OTHER INFORMATION: M2

<400> SEQUENCE: 44
cacaugucac gggguagg                                                 18

<210> SEQ ID NO 45
<211> LENGTH: 18
<212> TYPE: RNA
<213> ORGANISM: Artificial Sequence
<220> FEATURE:
<223> OTHER INFORMATION: M2

<400> SEQUENCE: 45
cacaugucac gggguagg                                                 18

<210> SEQ ID NO 46
<211> LENGTH: 17
<212> TYPE: RNA
<213> ORGANISM: Artificial Sequence
<220> FEATURE:
<223> OTHER INFORMATION: M2

<400> SEQUENCE: 46
cuacccucuu acuauug                                                  17

<210> SEQ ID NO 47
<211> LENGTH: 18
<212> TYPE: RNA
```

```
<213> ORGANISM: Artificial Sequence
<220> FEATURE:
<223> OTHER INFORMATION: M2

<400> SEQUENCE: 47
aauaguaugg cacaugug                                            18

<210> SEQ ID NO 48
<211> LENGTH: 16
<212> TYPE: RNA
<213> ORGANISM: Artificial Sequence
<220> FEATURE:
<223> OTHER INFORMATION: M2

<400> SEQUENCE: 48
cuacccucuu acuauu                                              16

<210> SEQ ID NO 49
<211> LENGTH: 17
<212> TYPE: RNA
<213> ORGANISM: Artificial Sequence
<220> FEATURE:
<223> OTHER INFORMATION: M2

<400> SEQUENCE: 49
aauaguaugg cacaugu                                             17

<210> SEQ ID NO 50
<211> LENGTH: 17
<212> TYPE: RNA
<213> ORGANISM: Artificial Sequence
<220> FEATURE:
<223> OTHER INFORMATION: M2

<400> SEQUENCE: 50
acaugucacg ggguagg                                             17

<210> SEQ ID NO 51
<211> LENGTH: 16
<212> TYPE: RNA
<213> ORGANISM: Artificial Sequence
<220> FEATURE:
<223> OTHER INFORMATION: M2

<400> SEQUENCE: 51
acaugucacg ggguag                                              16

<210> SEQ ID NO 52
<211> LENGTH: 15
<212> TYPE: RNA
<213> ORGANISM: Artificial Sequence
<220> FEATURE:
<223> OTHER INFORMATION: M2

<400> SEQUENCE: 52
uacccucuua cuauu                                               15

<210> SEQ ID NO 53
<211> LENGTH: 16
<212> TYPE: RNA
<213> ORGANISM: Artificial Sequence
<220> FEATURE:
<223> OTHER INFORMATION: M2

<400> SEQUENCE: 53
auaguauggc acaugu                                              16
```

```
<210> SEQ ID NO 54
<211> LENGTH: 14
<212> TYPE: RNA
<213> ORGANISM: Artificial Sequence
<220> FEATURE:
<223> OTHER INFORMATION: M2

<400> SEQUENCE: 54
uacccucuua cuau                                                      14

<210> SEQ ID NO 55
<211> LENGTH: 15
<212> TYPE: RNA
<213> ORGANISM: Artificial Sequence
<220> FEATURE:
<223> OTHER INFORMATION: M2

<400> SEQUENCE: 55
auaguauggc acaug                                                     15

<210> SEQ ID NO 56
<211> LENGTH: 15
<212> TYPE: RNA
<213> ORGANISM: Artificial Sequence
<220> FEATURE:
<223> OTHER INFORMATION: M2

<400> SEQUENCE: 56
caugucacgg gguag                                                     15

<210> SEQ ID NO 57
<211> LENGTH: 14
<212> TYPE: RNA
<213> ORGANISM: Artificial Sequence
<220> FEATURE:
<223> OTHER INFORMATION: M2

<400> SEQUENCE: 57
caugucacgg ggua                                                      14

<210> SEQ ID NO 58
<211> LENGTH: 13
<212> TYPE: RNA
<213> ORGANISM: Artificial Sequence
<220> FEATURE:
<223> OTHER INFORMATION: M2

<400> SEQUENCE: 58
acccucuuac uau                                                       13

<210> SEQ ID NO 59
<211> LENGTH: 14
<212> TYPE: RNA
<213> ORGANISM: Artificial Sequence
<220> FEATURE:
<223> OTHER INFORMATION: M2

<400> SEQUENCE: 59
uaguauggca caug                                                      14

<210> SEQ ID NO 60
<211> LENGTH: 12
<212> TYPE: RNA
<213> ORGANISM: Artificial Sequence
<220> FEATURE:
```

<223> OTHER INFORMATION: M2

<400> SEQUENCE: 60
acccucuuac ua                                                          12

<210> SEQ ID NO 61
<211> LENGTH: 13
<212> TYPE: RNA
<213> ORGANISM: Artificial Sequence
<220> FEATURE:
<223> OTHER INFORMATION: M2

<400> SEQUENCE: 61
uaguauggca cau                                                         13

<210> SEQ ID NO 62
<211> LENGTH: 13
<212> TYPE: RNA
<213> ORGANISM: Artificial Sequence
<220> FEATURE:
<223> OTHER INFORMATION: M2

<400> SEQUENCE: 62
augucacggg gua                                                         13

<210> SEQ ID NO 63
<211> LENGTH: 11
<212> TYPE: RNA
<213> ORGANISM: Artificial Sequence
<220> FEATURE:
<223> OTHER INFORMATION: M2

<400> SEQUENCE: 63
augucacggg g                                                           11

<210> SEQ ID NO 64
<211> LENGTH: 11
<212> TYPE: RNA
<213> ORGANISM: Artificial Sequence
<220> FEATURE:
<223> OTHER INFORMATION: M2

<400> SEQUENCE: 64
cccucuuacu a                                                           11

<210> SEQ ID NO 65
<211> LENGTH: 12
<212> TYPE: RNA
<213> ORGANISM: Artificial Sequence
<220> FEATURE:
<223> OTHER INFORMATION: M2

<400> SEQUENCE: 65
uaguauggca ca                                                          12

<210> SEQ ID NO 66
<211> LENGTH: 10
<212> TYPE: RNA
<213> ORGANISM: Artificial Sequence
<220> FEATURE:
<223> OTHER INFORMATION: M2

<400> SEQUENCE: 66
ugucacgggg                                                             10

```
<210> SEQ ID NO 67
<211> LENGTH: 9
<212> TYPE: RNA
<213> ORGANISM: Artificial Sequence
<220> FEATURE:
<223> OTHER INFORMATION: M2

<400> SEQUENCE: 67 ugucacggg                                                              9

<210> SEQ ID NO 68
<211> LENGTH: 10
<212> TYPE: RNA
<213> ORGANISM: Artificial Sequence
<220> FEATURE:
<223> OTHER INFORMATION: M2

<400> SEQUENCE: 68
ccucuuacua                                                            10

<210> SEQ ID NO 69
<211> LENGTH: 17
<212> TYPE: RNA
<213> ORGANISM: Artificial Sequence
<220> FEATURE:
<223> OTHER INFORMATION: M2

<400> SEQUENCE: 69
cacaugucac gggguag                                                    17

<210> SEQ ID NO 70
<211> LENGTH: 16
<212> TYPE: RNA
<213> ORGANISM: Artificial Sequence
<220> FEATURE:
<223> OTHER INFORMATION: M2

<400> SEQUENCE: 70
cacaugucac ggggua                                                     16

<210> SEQ ID NO 71
<211> LENGTH: 12
<212> TYPE: RNA
<213> ORGANISM: Artificial Sequence
<220> FEATURE:
<223> OTHER INFORMATION: M2

<400> SEQUENCE: 71
caugucacgg gg                                                         12

<210> SEQ ID NO 72
<211> LENGTH: 12
<212> TYPE: RNA
<213> ORGANISM: Artificial Sequence
<220> FEATURE:
<223> OTHER INFORMATION: M2

<400> SEQUENCE: 72
cccucuuacu au                                                         12

<210> SEQ ID NO 73
<211> LENGTH: 10
<212> TYPE: RNA
<213> ORGANISM: Artificial Sequence
<220> FEATURE:
<223> OTHER INFORMATION: M2
```

```
<400> SEQUENCE: 73
aguauggcac                                                              10

<210> SEQ ID NO 74
<211> LENGTH: 8
<212> TYPE: RNA
<213> ORGANISM: Artificial Sequence
<220> FEATURE:
<223> OTHER INFORMATION: M2

<400> SEQUENCE: 74 gucacggg                                                                 8

<210> SEQ ID NO 75
<211> LENGTH: 8
<212> TYPE: RNA
<213> ORGANISM: Artificial Sequence
<220> FEATURE:
<223> OTHER INFORMATION: M2

<400> SEQUENCE: 75 ccucuuac                                                                 8

<210> SEQ ID NO 76
<211> LENGTH: 18
<212> TYPE: RNA
<213> ORGANISM: Artificial Sequence
<220> FEATURE:
<223> OTHER INFORMATION: SF5

<400> SEQUENCE: 76
gcuaauguau guguccg                                                      18

<210> SEQ ID NO 77
<211> LENGTH: 16
<212> TYPE: RNA
<213> ORGANISM: Artificial Sequence
<220> FEATURE:
<223> OTHER INFORMATION: SF5

<400> SEQUENCE: 77
cuaauguaug uugucc                                                       16

<210> SEQ ID NO 78
<211> LENGTH: 18
<212> TYPE: RNA
<213> ORGANISM: Artificial Sequence
<220> FEATURE:
<223> OTHER INFORMATION: SF5

<400> SEQUENCE: 78
ggacagcagg ggagcgug                                                     18

<210> SEQ ID NO 79
<211> LENGTH: 16
<212> TYPE: RNA
<213> ORGANISM: Artificial Sequence
<220> FEATURE:
<223> OTHER INFORMATION: SF5

<400> SEQUENCE: 79
cacacucuug cauuag                                                       16

<210> SEQ ID NO 80
<211> LENGTH: 14
```

```
<212> TYPE: RNA
<213> ORGANISM: Artificial Sequence
<220> FEATURE:
<223> OTHER INFORMATION: SF5

<400> SEQUENCE: 80
uaauguaugu uguc                                                         14

<210> SEQ ID NO 81
<211> LENGTH: 16
<212> TYPE: RNA
<213> ORGANISM: Artificial Sequence
<220> FEATURE:
<223> OTHER INFORMATION: SF5

<400> SEQUENCE: 81
gacagcaggg gagcgu                                                       16

<210> SEQ ID NO 82
<211> LENGTH: 14
<212> TYPE: RNA
<213> ORGANISM: Artificial Sequence
<220> FEATURE:
<223> OTHER INFORMATION: SF5

<400> SEQUENCE: 82
acacucuugc auua                                                         14

<210> SEQ ID NO 83
<211> LENGTH: 12
<212> TYPE: RNA
<213> ORGANISM: Artificial Sequence
<220> FEATURE:
<223> OTHER INFORMATION: SF5

<400> SEQUENCE: 83
aauguauguu gu                                                           12

<210> SEQ ID NO 84
<211> LENGTH: 14
<212> TYPE: RNA
<213> ORGANISM: Artificial Sequence
<220> FEATURE:
<223> OTHER INFORMATION: SF5

<400> SEQUENCE: 84
acagcagggg agcg                                                         14

<210> SEQ ID NO 85
<211> LENGTH: 12
<212> TYPE: RNA
<213> ORGANISM: Artificial Sequence
<220> FEATURE:
<223> OTHER INFORMATION: SF5

<400> SEQUENCE: 85
cacucuugca uu                                                           12

<210> SEQ ID NO 86
<211> LENGTH: 10
<212> TYPE: RNA
<213> ORGANISM: Artificial Sequence
<220> FEATURE:
<223> OTHER INFORMATION: SF5

<400> SEQUENCE: 86
```
auguauguug                                                                    10

<210> SEQ ID NO 87
<211> LENGTH: 12
<212> TYPE: RNA
<213> ORGANISM: Artificial Sequence
<220> FEATURE:
<223> OTHER INFORMATION: SF5

<400> SEQUENCE: 87
cagcagggga gc                                                                 12

<210> SEQ ID NO 88
<211> LENGTH: 10
<212> TYPE: RNA
<213> ORGANISM: Artificial Sequence
<220> FEATURE:
<223> OTHER INFORMATION: SF5

<400> SEQUENCE: 88
acucuugcau                                                                    10

<210> SEQ ID NO 89
<211> LENGTH: 19
<212> TYPE: RNA
<213> ORGANISM: Artificial Sequence
<220> FEATURE:
<223> OTHER INFORMATION: SF5

<400> SEQUENCE: 89
cggacagcag ggagcgugc                                                          19

<210> SEQ ID NO 90
<211> LENGTH: 17
<212> TYPE: RNA
<213> ORGANISM: Artificial Sequence
<220> FEATURE:
<223> OTHER INFORMATION: SF5

<400> SEQUENCE: 90
cuaauguaug ugugucc                                                            17

<210> SEQ ID NO 91
<211> LENGTH: 17
<212> TYPE: RNA
<213> ORGANISM: Artificial Sequence
<220> FEATURE:
<223> OTHER INFORMATION: SF5

<400> SEQUENCE: 91
ggacagcagg gagcgug                                                            17

<210> SEQ ID NO 92
<211> LENGTH: 15
<212> TYPE: RNA
<213> ORGANISM: Artificial Sequence
<220> FEATURE:
<223> OTHER INFORMATION: SF5

<400> SEQUENCE: 92
uaauguaugu guguc                                                              15

<210> SEQ ID NO 93
<211> LENGTH: 15
<212> TYPE: RNA
<213> ORGANISM: Artificial Sequence

```
<220> FEATURE:
<223> OTHER INFORMATION: SF5

<400> SEQUENCE: 93
gacagcaggg agcgu                                                        15

<210> SEQ ID NO 94
<211> LENGTH: 13
<212> TYPE: RNA
<213> ORGANISM: Artificial Sequence
<220> FEATURE:
<223> OTHER INFORMATION: SF5

<400> SEQUENCE: 94
aauguaugug ugu                                                          13

<210> SEQ ID NO 95
<211> LENGTH: 13
<212> TYPE: RNA
<213> ORGANISM: Artificial Sequence
<220> FEATURE:
<223> OTHER INFORMATION: SF5

<400> SEQUENCE: 95
acagcaggga gcg                                                          13

<210> SEQ ID NO 96
<211> LENGTH: 12
<212> TYPE: RNA
<213> ORGANISM: Artificial Sequence
<220> FEATURE:
<223> OTHER INFORMATION: SF5

<400> SEQUENCE: 96
cacucuugca uu                                                           12

<210> SEQ ID NO 97
<211> LENGTH: 11
<212> TYPE: RNA
<213> ORGANISM: Artificial Sequence
<220> FEATURE:
<223> OTHER INFORMATION: SF5

<400> SEQUENCE: 97
auguaugugu g                                                            11

<210> SEQ ID NO 98
<211> LENGTH: 11
<212> TYPE: RNA
<213> ORGANISM: Artificial Sequence
<220> FEATURE:
<223> OTHER INFORMATION: SF5

<400> SEQUENCE: 98
cagcagggag c                                                            11

<210> SEQ ID NO 99
<211> LENGTH: 13
<212> TYPE: RNA
<213> ORGANISM: Artificial Sequence
<220> FEATURE:
<223> OTHER INFORMATION: GA1

<400> SEQUENCE: 99
uauaggcugu gca                                                          13
```

```
<210> SEQ ID NO 100
<211> LENGTH: 11
<212> TYPE: RNA
<213> ORGANISM: Artificial Sequence
<220> FEATURE:
<223> OTHER INFORMATION: GA1

<400> SEQUENCE: 100
ugacagguug u                                                            11

<210> SEQ ID NO 101
<211> LENGTH: 11
<212> TYPE: RNA
<213> ORGANISM: Artificial Sequence
<220> FEATURE:
<223> OTHER INFORMATION: GA1

<400> SEQUENCE: 101
gcaauacuau a                                                            11

<210> SEQ ID NO 102
<211> LENGTH: 10
<212> TYPE: RNA
<213> ORGANISM: Artificial Sequence
<220> FEATURE:
<223> OTHER INFORMATION: Phi29
<220> FEATURE:
<221> NAME/KEY: misc_RNA
<222> LOCATION: (1)..(10)
<223> OTHER INFORMATION: W represents A, C, G and U nucleotides which
      form pairs according to canonical Watson-Crick base pairing, or
      non-canonical base pairing in the assembled 3WJ construct

<400> SEQUENCE: 102 wwwwwwwwww                                                              10

<210> SEQ ID NO 103
<211> LENGTH: 11
<212> TYPE: RNA
<213> ORGANISM: Artificial Sequence
<220> FEATURE:
<223> OTHER INFORMATION: Phi29
<220> FEATURE:
<221> NAME/KEY: misc_RNA
<222> LOCATION: (1)..(11)
<223> OTHER INFORMATION: N represents A, C, G, and U nucleotides which
      are unpaired in the assembled 3WJ construct
<220> FEATURE:
<221> NAME/KEY: misc_feature
<222> LOCATION: (6)..(6)
<223> OTHER INFORMATION: n is a, c, g, or u

<400> SEQUENCE: 103
cccccncccc c                                                            11

<210> SEQ ID NO 104
<211> LENGTH: 10
<212> TYPE: RNA
<213> ORGANISM: Artificial Sequence
<220> FEATURE:
<223> OTHER INFORMATION: Phi29
<220> FEATURE:
<221> NAME/KEY: misc_RNA
<222> LOCATION: (1)..(10)
<223> OTHER INFORMATION: W represents A, C, G and U nucleotides which
      form pairs according to canonical Watson-Crick base pairing, or
      non-canonical base pairing in the assembled 3WJ construct

<400> SEQUENCE: 104
```
wwwwwccccc                                                              10

<210> SEQ ID NO 105
<211> LENGTH: 10
<212> TYPE: RNA
<213> ORGANISM: Artificial Sequence
<220> FEATURE:
<223> OTHER INFORMATION: M2
<220> FEATURE:
<221> NAME/KEY: misc_RNA
<222> LOCATION: (1)..(10)
<223> OTHER INFORMATION: Nucleotides form pairs according to canonical
      Watson-Crick base pairing, or non-canonical base pairing in the
      assembled 3WJ construct

<400> SEQUENCE: 105
ccccccccc                                                               10

<210> SEQ ID NO 106
<211> LENGTH: 11
<212> TYPE: RNA
<213> ORGANISM: Artificial Sequence
<220> FEATURE:
<223> OTHER INFORMATION: M2
<220> FEATURE:
<221> NAME/KEY: misc_RNA
<222> LOCATION: (1)..(11)
<223> OTHER INFORMATION: W represents A, C, G and U nucleotides which
      form pairs according to canonical Watson-Crick base pairing, or
      non-canonical base pairing in the assembled 3WJ construct. N
      represents A, C, G, and U nucleotides which are unpaired in the
      assembled 3WJ co
<220> FEATURE:
<221> NAME/KEY: misc_RNA
<222> LOCATION: (1)..(11)
<223> OTHER INFORMATION: W represents A, C, G and U nucleotides which
      form pairs according to canonical Watson-Crick base pairing, or
      non-canonical base pairing in the assembled 3WJ construct. N
      represents A, C, G, and U nucleotides which are unpaired in the
      assembled 3WJ construct
<220> FEATURE:
<221> NAME/KEY: misc_feature
<222> LOCATION: (6)..(6)
<223> OTHER INFORMATION: n is a, c, g, or u

<400> SEQUENCE: 106 wwwwwnccc c                                                             11

<210> SEQ ID NO 107
<211> LENGTH: 12
<212> TYPE: RNA
<213> ORGANISM: Artificial Sequence
<220> FEATURE:
<223> OTHER INFORMATION: M2
<220> FEATURE:
<221> NAME/KEY: misc_RNA
<222> LOCATION: (1)..(12)
<223> OTHER INFORMATION: W represents A, C, G and U nucleotides which
      form pairs according to canonical Watson-Crick base pairing, or
      non-canonical base pairing in the assembled 3WJ construct. N
      represents A, C, G, and U nucleotides which are unpaired in the
      assembled 3WJ construct
<220> FEATURE:
<221> NAME/KEY: misc_feature
<222> LOCATION: (10)..(10)
<223> OTHER INFORMATION: n is a, c, g, or u

<400> SEQUENCE: 107 wwwwwwwwn ww                                                            12

<210> SEQ ID NO 108
<211> LENGTH: 12

-continued

```
<212> TYPE: RNA
<213> ORGANISM: Artificial Sequence
<220> FEATURE:
<223> OTHER INFORMATION: SF5
<220> FEATURE:
<221> NAME/KEY: misc_RNA
<222> LOCATION: (1)..(12)
<223> OTHER INFORMATION: W represents A, C, G and U nucleotides which
      form pairs according to canonical Watson-Crick base pairing, or
      non-canonical base pairing in the assembled 3WJ construct. N
      represents A, C, G, and U nucleotides which are unpaired in the
      assembled 3WJ construct
<220> FEATURE:
<221> NAME/KEY: misc_feature
<222> LOCATION: (6)..(7)
<223> OTHER INFORMATION: n is a, c, g, or u

<400> SEQUENCE: 108
wwwwwnnccc cc                                                         12

<210> SEQ ID NO 109
<211> LENGTH: 11
<212> TYPE: RNA
<213> ORGANISM: Artificial Sequence
<220> FEATURE:
<223> OTHER INFORMATION: SF5
<220> FEATURE:
<221> NAME/KEY: misc_RNA
<222> LOCATION: (1)..(11)
<223> OTHER INFORMATION: W represents A, C, G and U nucleotides which
      form pairs according to canonical Watson-Crick base pairing, or
      non-canonical base pairing in the assembled 3WJ construct. N
      represents A, C, G, and U nucleotides which are unpaired in the
      assembled 3WJ construct
<220> FEATURE:
<221> NAME/KEY: misc_feature
<222> LOCATION: (9)..(9)
<223> OTHER INFORMATION: n is a, c, g, or u

<400> SEQUENCE: 109 wwwwwwwnw w                                                           11

<210> SEQ ID NO 110
<211> LENGTH: 12
<212> TYPE: RNA
<213> ORGANISM: Artificial Sequence
<220> FEATURE:
<223> OTHER INFORMATION: SF5
<220> FEATURE:
<221> NAME/KEY: misc_RNA
<222> LOCATION: (1)..(12)
<223> OTHER INFORMATION: N represents A, C, G, and U nucleotides which
      are unpaired in the assembled 3WJ construct
<220> FEATURE:
<221> NAME/KEY: misc_feature
<222> LOCATION: (6)..(7)
<223> OTHER INFORMATION: n is a, c, g, or u

<400> SEQUENCE: 110
cccccnnccc cc                                                         12
```

What is claimed is:

1. An RNA junction scaffold, comprising: a three-way junction (3WJ) domain, the 3WJ domain comprising a 3WJa sequence comprising a first RNA polynucleotide, a 3WJb sequence comprising a second RNA polynucleotide, and a 3WJc sequence comprising a third RNA polynucleotide, wherein a first branch of the 3WJ domain is formed from a 5' portion of the 3WJa sequence and a 3' portion of the 3WJc sequence and comprises a first helical region, a second branch of the 3WJ domain is formed from a 3' portion of the 3WJa sequence and a 5' portion of the 3WJb sequence and comprises a second helical region, and a third branch of the 3WJ domain is formed from a 3' portion of the 3WJb sequence and a 5' portion of the 3WJc sequence and comprises a third helical region, wherein each of said helical regions comprises a plurality of RNA nucleotide pairs that form canonical Watson-Crick bonds, and wherein (i) the 3WJa sequence is absent an unpaired nucleotide positioned between the first helical region and the second helical region, and two unpaired nucleotides are positioned in the 3WJa sequence in the second branch, and (ii) two adjacent unpaired nucleotides are positioned in the 3WJc sequence between the first helical region and the third helical region, and one unpaired nucleotide is positioned in the 3WJb sequence between the second helical region and the third helical region.

2. The RNA junction scaffold of claim 1, wherein the 3WJa sequence comprises SEQ ID NO:73, the 3WJb sequence comprises SEQ ID NO:74, and the 3WJc sequence comprises SEQ ID NO:75.

3. The RNA junction scaffold of claim 1, wherein the second branch is absent adjacent unpaired nucleotides in positions corresponding to unpaired adenine and uracil nucleotides in positions 36 and 37, respectively, of a wild type M2 pRNA, and wherein the third branch is absent an unpaired nucleotide in a position corresponding to an unpaired adenine nucleotide in position 79 of said wild type M2 pRNA.

4. The RNA junction scaffold of claim 1, absent one or more unpaired nucleotides in the 3WJa sequence downstream of the two unpaired nucleotides present in the 3WJa sequence.

5. The RNA junction scaffold of claim 1, absent an unpaired nucleotide in the 3WJb sequence downstream of the unpaired nucleotide present in the 3WJb sequence.

6. The RNA junction scaffold of claim 1, absent one or more unpaired nucleotides in the 3WJa sequence downstream of the two unpaired nucleotides present in the 3WJa sequence, and absent an unpaired nucleotide in the 3WJb sequence downstream of the unpaired nucleotide present in the 3WJb sequence.

7. A conjugate comprising the RNA 3WJ scaffold of claim 1, linked to at least one moiety selected from the group consisting of therapeutic drugs, antibodies, markers, dyes, siRNAs, ribozymes, riboswitches, and aptamers.

8. A composition, comprising the conjugate of claim 7, and a pharmaceutically-acceptable vehicle, carrier, or diluent.

9. An RNA junction scaffold, comprising: a three-way junction (3WJ) domain, the 3WJ domain comprising a 3WJa sequence comprising a first RNA polynucleotide, a 3WJb sequence comprising a second RNA polynucleotide, and a 3WJc sequence comprising a third RNA polynucleotide, wherein a first branch of the 3WJ domain is formed from a 5' portion of the 3WJa sequence and a 3' portion of the 3WJc sequence and comprises a first helical region, a second branch of the 3WJ domain is formed from a 3' portion of the 3WJa sequence and a 5' portion of the 3WJb sequence and comprises a second helical region, and a third branch of the 3WJ domain is formed from a 3' portion of the 3WJb sequence and a 5' portion of the 3WJc sequence and comprises a third helical region, wherein each of said helical regions comprises a plurality of RNA nucleotide pairs that form canonical Watson-Crick bonds, and wherein (i) the 3WJa sequence comprises zero or one unpaired nucleotide positioned between the first helical region and the second helical region, and/or one or two unpaired nucleotides in the second branch, and (ii) the 3WJc sequence comprises one unpaired or two adjacent unpaired nucleotides between the first helical region and the third helical region, and/or the 3WJb sequence comprises up to two unpaired nucleotides selected from the group consisting of one unpaired nucleotide and two adjacent unpaired nucleotides, wherein the up to two unpaired nucleotides are positioned in the 3WJb sequence between the second helical region and the third helical region.

10. A conjugate comprising the RNA 3WJ scaffold of claim 9, linked to at least one moiety selected from the group consisting of therapeutic drugs, antibodies, markers, dyes, siRNAs, ribozymes, riboswitches, and aptamers.

11. A composition, comprising the conjugate of claim 9, and a pharmaceutically-acceptable vehicle, carrier, or diluent.

12. The RNA junction scaffold of claim 9, wherein each of the 3WJa, 3WJb, and 3WJc sequences comprises, independently, from 8 to 36 nucleotides, not including an RNA linker or an RNA portion of a biologically-active moiety conjugated to the RNA scaffold.

\* \* \* \* \*